US00RE46837E

(19) United States
(12) Reissued Patent
Tyers et al.

(10) Patent Number: US RE46,837 E
(45) Date of Reissued Patent: May 8, 2018

(54) SECONDARY HEADER FOR AN IMPLANTABLE MEDICAL DEVICE INCORPORATING AN ISO DF4 CONNECTOR AND CONNECTOR CAVITY AND/OR AN IS4 CONNECTOR AND CONNECTOR CAVITY

(71) Applicant: Greatbatch Ltd., Clarence, NY (US)

(72) Inventors: Geddes Frank Owen Tyers, Vancouver (CA); Robert A. Stevenson, Canyon Country, CA (US); Christina A. Frysz, Orchard Park, NY (US)

(73) Assignee: Greatbatch Ltd., Clarence, NY (US)

(21) Appl. No.: 15/058,470

(22) Filed: Mar. 2, 2016

Related U.S. Patent Documents

Reissue of:
(64) Patent No.: 8,543,209
Issued: Sep. 24, 2013
Appl. No.: 13/413,463
Filed: Mar. 6, 2012

U.S. Applications:
(60) Provisional application No. 61/449,790, filed on Mar. 7, 2011.

(51) Int. Cl.
*A61N 1/00* (2006.01)
*H01R 27/02* (2006.01)
(Continued)

(52) U.S. Cl.
CPC ..... *H01R 27/02* (2013.01); *A61N 1/3752* (2013.01); *H01R 31/065* (2013.01); *H01R 24/58* (2013.01); *H01R 2201/12* (2013.01)

(58) Field of Classification Search
CPC ..... A61N 1/362; A61N 1/372; A61N 1/375; A61N 1/3752; H01R 24/58; H01R 13/5224; H01R 31/06
See application file for complete search history.

(56) References Cited

U.S. PATENT DOCUMENTS 5,679,026 A * 10/1997 Fain ..... A61N 1/3752 439/651
5,919,213 A * 7/1999 Nelson ..... A61N 1/372 607/8

(Continued)

FOREIGN PATENT DOCUMENTS

EP 2497532 9/2012

OTHER PUBLICATIONS

European Search Report dated Jul. 5, 2012.
Extended European Search Report for 12158362.9 dated Jun. 5, 2013.

*Primary Examiner* — Catherine S Williams
(74) *Attorney, Agent, or Firm* — Michael F. Scalise

(57) ABSTRACT

A secondary header for an active implantable medical device (AIMD) incorporates a secondary header plug configured for mating insertion into an AIMD ISO DF4 or IS4 connector cavity, a secondary header ISO DF4 or IS4 connector cavity, and at least one replacement lead connector cavity. The secondary header plug has four electrical contacts which correspond to four electrical contacts of the AIMD connector cavity. The secondary header connector cavity has less than four electrical contacts conductively coupled to the secondary header plug electrical contacts. The replacement lead connector cavity has at least one electrical contact conductively coupled to at least one electrical contact of the secondary header plug. An intermediate conformal section between the secondary header plug and a housing for the secondary header connector cavity places the secondary header connector cavity housing adjacent to an exterior surface of the AIMD.

44 Claims, 26 Drawing Sheets

(51) Int. Cl.

| | |
|---|---|
| ***H01R 31/06*** | (2006.01) |
| ***A61N 1/375*** | (2006.01) |
| *H01R 24/58* | (2011.01) |

(56) References Cited

U.S. PATENT DOCUMENTS

| | | | | |
|---|---|---|---|---|
| 6,743,055 | B1 * | 6/2004 | Flynn | A61N 1/3752 439/651 |
| 7,128,600 | B2 | 10/2006 | Osypka et al. | |
| 7,225,034 | B2 * | 5/2007 | Ries et al. | 607/122 |
| 8,000,801 | B2 | 8/2011 | Stevenson et al. | |
| 8,200,342 | B2 | 6/2012 | Stevenson et al. | |
| 8,374,695 | B2 | 2/2013 | McDonald et al. | |
| 8,600,509 | B2 | 12/2013 | McDonald et al. | |
| 2004/0260373 | A1 | 12/2004 | Ries et al. | |
| 2010/0070009 | A1 | 3/2010 | Barker | |
| 2010/0137956 | A1 | 6/2010 | Osypka | |
| 2010/0174349 | A1 | 7/2010 | Stevenson et al. | |
| 2011/0022140 | A1 * | 1/2011 | Stevenson et al. | 607/116 |
| 2011/0029052 | A1 | 2/2011 | McDonald et al. | |

* cited by examiner

SECONDARY HEADER FOR AN IMPLANTABLE MEDICAL DEVICE INCORPORATING AN ISO DF4 CONNECTOR AND CONNECTOR CAVITY AND/OR AN IS4 CONNECTOR AND CONNECTOR CAVITY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF INVENTION

This invention generally relates to a secondary header for active implantable medical devices (AIMDs). More specifically, this invention relates to header adaptors for use with active implantable medical devices such as, cardiac pacemakers, implantable cardioverter defibrillators (ICD), cardiac resynchronization therapy (CRT) devices, neurostimulators and related leads. In a preferred embodiment, the invention facilitates connection of an additional lead or multiple medical leads, in the case where one or more of the lead conductors of a previously implanted lead such as a DF4 or IS4 lead has failed while retaining the still functional components of the partially failed or dysfunctional lead via reconnection through this secondary header.

BACKGROUND OF THE INVENTION

Transvenous cardiac pacemakers and ICDs using leads threaded into the right sided chambers of the heart through the venous system have evolved over the years from single chamber (one implanted lead) to dual chamber (two implanted leads); then to single and eventually dual chamber ICDs. More recently with the wider recognition of the increased incidence of heart failure secondary to right sided pacing of the heart, as well to numerous other etiologies CRT devices have been developed with left sided chamber leads delivered transvenously to endocardial locations, and/or on through the coronary sinus to left ventricular epicardial locations, and/or with a variety of transthoracic approaches to direct epicardial or intramyocardial left ventricular or left atrial stimulation sites.

In a typical prior art dual chamber defibrillator system, there is a trifurcated ventricular lead connector, with one arm providing low voltage IS-1 pace-sense function and two arms providing high voltage DF-1 connections. An advantage of this configuration was that if one of the high voltage or low voltage components of this type of lead failed, it could be corrected relatively simply by implanting a replacement single function lead, disconnecting the failed component from the pulse generator header and plugging the replacement lead's connector into that connector cavity thereby abandoning the failed lead. However, along with the AIMD, the trifurcated connector considerably increased the mass in a patient's pectoral (or other) pocket, provided the opportunity for cross connections at the time of initial implant, plus was prone to failure and increased the difficulty and risks associated with subsequent pulse generator or lead replacement/repair surgery.

The ISO 27186 Standard for DF4 and IS4 quadripolar connector systems evolved in order to replace the mechanically and functionally complex trifurcated connector with a single lead connector encompassing multiple sequential electrodes and functions, and requiring only a single set screw for lead fixation and electrical activation of the pin electrode. This minimized the number of connector cavities in, and size of, defibrillator headers simplified surgical implant procedures and reduced the risk of technical errors. However, lead conductor failures, particularly of IS4 and DF4 style leads have occurred.

Furthermore, it is not always practical to extract an IS4 or DF4 lead even if a single conductor or function has failed. The lead extraction procedure becomes particularly more difficult as the duration of implantation lengthens. Over time, the lead typically becomes adhered to tissue due to the formation of scar tissue, tissue ingrowth and the like thus requiring a more invasive procedure to be performed. Also, simply abandoning a defective IS4 or DF4 lead is problematic, because abandoning the old lead and implanting a new one can lead to venous occlusion and interference with closure of the tricuspid valve leaflets etc. Further, stacked ICD leads with large surface area high voltage coil electrodes tend to induce significant fibrous tissue reaction, binding the leads together and to surrounding tissues, and making extraction procedures even more hazardous. Yet extraction may in some cases become unavoidable because of the development of endocarditis or other complications.

Accordingly, there is a need for a novel secondary header or adaptor that facilitates restored functionality of a partially or completely dysfunctional lead and offers the added benefit of a low profile. These secondary headers or adaptors are indicated when one or more components of an implanted medical lead, particularly a DF4 or IS4 lead, has failed or become partially dysfunctional.

Failure of a medical lead conductor(s) can occur for a variety of reasons, including dislodgement at or migration from the electrode-tissue interface, complete or partial fracture or breakage of a lead conductor, abrasion or cracking or other forms of lead insulation disruption leading to low insulation resistance and low impedance measurements. Low insulation resistance can occur between a lead conductor and body fluid or between a lead conductor and adjacent lead conductors. Other reasons for failure include an increase in lead conductor impedance, an increase of the pacing capture threshold, or just the failure to deliver appropriate, effective or optimal therapy. As defined herein, a lead conductor failure may include one or more of any of the aforementioned conditions.

Adaptors of the prior art are generally of a relatively simple lead based design. They extend out into tissues away from the pulse generator pocket so that the distally inserted lead connectors are often well away from the pulse generator pocket at the time of subsequent reoperation; and even though inoperative attempts are made to wrap the added length of the adaptor and now surplus proximal lead body segments around the pulse generator and position the tangle of insulated wires behind it, postoperatively sections of insulative conductor are often prominent just beneath the skin. Patients often complain of what they feel is a doubling of implant bulk. In general, implanters fervently dislike lead based adaptors because of the mish mash of crossing conductors from the attached leads and the adaptor itself can be a nightmare to dissect out at reoperation, maximizing the probability of intraprocedural damage during reoperation. The additional electrical connections focus stresses and conductor and insulation failure are common. Stimulation of adjacent chest wall musculature is also common because of multiple poorly insulated set screw connections.

Incorporation of the low and high voltage contacts of an older trifurcated connector defibrillator lead into the newer single DF4 (or its low voltage IS4 counterpart) has a number of functional limitations, but physically DF4 is a great improvement as it: (1) reduces the total volume of the implantable system; (2) reduces the number of set screws required to connect the lead to the defibrillator; (3) reduces the need for tissue dissection within the pocket during replacement; (4) reduces lead-on-lead interactions within the implant site or pocket; and (5) eliminates the potential for DF-1 connectors from being reversed in the defibrillator header. However all of these mechanical and procedural advantages are essentially lost if there is a failure of one of the multiple lead conductors, insulation (and/or their associated electrodes) either through damage or failure to deliver effective therapy.

A failure of one lead conductor in a DF4 system leaves the physician with several bad choices. The physician can put the patient, themselves and their surgical team through a potentially difficult lead explant/extraction surgery and then put in a new DF4 lead. This is not without significant risk. Or, the implanting physician could throw away the still functional defibrillator pulse generator and try to obtain a custom replacement pulse generator with all the original connector cavities including DF4, plus an additional DF-1 connector cavity for a case where a high voltage shocking coil component of the multifunctional lead system has failed, or, plus an additional IS-1 connector cavity where a component of the low voltage pace sense multifunctional lead system has failed. If this type of device was obtainable the physician could then plug the partially defective DF4 lead connector into the new DF4 header connector cavity, implant a new DF-1 lead or IS-1 lead, as indicated and in parallel with the pre-existing DF4 lead system, and insert it into the new header's additional DF-1 or IS-1 connector cavity. However, the new ICD would cost over $20,000 and would need to be specific to not only the DF4 component failure at hand, but also to the specific subtype of ICD being replaced, i.e., single chamber, dual chamber or resynchronization. Further, to date no manufacturer has agreed to produce the series of at least 6 custom ICDs necessary to repair all combinations of lead malfunction and ICD subtypes. The cost of maintaining the whole range of replacement devices in inventory would also be high.

And even if all these issues were overcome another problem would remain. That is, the defective lead is still in place and connected to the pulse generator circuits. The sine qua non of ICD lead failure, in addition to failure of therapeutic pace-sense or defibrillation functions, which the new ICD pulse generator and lead can correct, is inappropriate and on occasion involves lethal low impedance and high intensity shocks in the 100s of volts range. By inappropriate it is indicated that the patient is shocked, often repeatedly, not because a life threatening arrhythmia has occurred but because the defibrillator sensing circuits are receiving high rate signals generated from sites of insulation failure and or from conductor fractures in the original ICD leads low voltage/pace sense components. Alternatively, if the failure had occurred in the high voltage components of the DF4 lead, the potential for short-circuiting of required life saving shocks would persist. Prior art abandoned lead components can also be problematic during MRI scans because they can pick up high-power RF induced energy which can lead to overheating of the lead and/or its distal electrode, which can heat up or even burn surrounding heart tissue.

Reference is made to U.S. Pat. Nos. 7,225,034 and 7,242,987, the contents of which are incorporated herein by reference. These patents describe a lead-based adaptor for use with DF4 pulse generators at the time of ICD and lead system initial implantation, when defibrillation thresholds indicate an inadequate safety margin. These adaptors are similar in design to prior art products in that a connector, in this case DF4, is disposed at one end and connects into an elongated insulated, lead body like segment containing 4 lead wires. This eventually bifurcates into two arms, one terminating in a DF-1 connector cavity and the other terminating in a DF4 connector cavity. This allows reuse of the DF4 lead and parallel hard wired cross connection of one or more of the high voltage outputs to one or more additional DF-1 leads to see if an improved shock vector can be obtained. The adaptors described in these patents introduce all of the previously described disadvantages and concerns related to adaptors in general but in addition will further greatly increase the bulk of a pectoral or other pocket. The '034 and '987 patents are not directed to a situation where a previously implanted lead conductor has failed. These patents are directed towards supplying additional connector cavities if additional defibrillation vectors are required and are not relevant to the post implant repair of a high voltage shocking coil or failed pace sense functions There is no provision within the '034 patent, for example, to disconnect defective lead component or components, and prevent them from interfering with sensitive AIMD circuitry and functions. FIG. 3 of the '987 patent does show a switch 110 which provides a means for reversibly decoupling the proximal high voltage electrode of the first DF4 lead from the high voltage electrode of the supplemental DF-1 lead, but this is neither permanent nor reliable, and introduction of a somewhat rigid switch component into the grip zone or lead like body of the adaptor would add complexity and focus flexural stresses with increased probability of fracture of adjacent conductors. The FIG. 3 drawing description of the '987 patent states that, "When defibrillation thresholds achieved using coil electrodes on a first lead, for example electrodes 54 and 52 of said lead 40 shown in FIG. 1, are unacceptably high such that placement of a second high-voltage lead, for example, lead 60, is required, it may be desirable to provide a high-voltage signal to the second lead without providing the same high-voltage signal to a coil electrode on the first lead. As such, switch 110 is provided between connector ring 28 and conductor 78A or anywhere along conductor 78A, which is coupled to contact 86 as shown previously in FIG. 2." In other words, the switch of the '987 patent is directed towards optimizing therapeutic defibrillation vectors. As used in the '987 patent, the word signal refers to a high-voltage biphasic or monophasic defibrillation shock. Nowhere in the '034 or '987 patents is the problem of a previously implanted damaged or defective lead conductor or other component addressed, nor is provision made to provide a header adaptor to be able to cope with this. And, as with all prior art adaptors, such as from Oscor, or Medtronic such as described in the '034 and '987 patents, are lead based. This means that the bifurcated connector cavity terminals for receiving the bulky DF4 connector and the added DF-1 lead connector are located several centimeters along a lead away from the pulse generator. Accordingly, the pectoral or alternative site, pocket bulk is increased and all the other lead based adaptor disadvantages are preserved. In addition, the '987 and '034 patents lead-based adaptors have all of the same problems as previously described for prior art leads with trifurcated lead connectors wherein, subsequent surgery and removal of the device can be problematic. One may also go to the website of Oscor Incorporated to see an entire family of lead-based adaptors.

As previously stated, lead conductors can fail for a variety of reasons. Conductor failures and recalls of implanted leads have been common in the implantable medical device industry. An interesting exercise is to do a simple Google search using the following key words: "pacemaker lead recalls." Literally, hundreds of "hits" come up. It has been common in the implantable medical device industry to abandon a defective lead and simply implant a new one roughly in parallel with it through the venous system.

There are a number of problems with abandoned leads, including the problem of MRI RF field-induced overheating of such a lead or its distal electrode. Implanted leads are generally less dangerous when they are connected to a pulse generator (as in the '987 and '034 patents except for the switch being open). The reason for this is that prior art pulse generators, including pacemakers and defibrillators generally have a feedthrough filter capacitor at the point of lead conductor ingress through the hermetic seal of the active implantable medical device. At high frequencies, such as for MRI RF pulsed frequencies, this EMI filter provides a low impedance path between the lead conductors and the AIMD housing which acts as an energy dissipating surface. Accordingly, in a high power MRI environment, much of the RF energy that is induced in the lead is diverted by the feedthrough capacitor where it is dissipated as a small temperature rise on the relatively large surface area of the pacemaker housing, which is usually a titanium can. However, when a lead is abandoned, there is no place for this MRI RF energy to go other than at the distal tip electrode, which can still be in contact with biological cells. This can lead to significant overheating. For additional information regarding the danger of abandoned lead conductors, one is referred to a published paper entitled, PACEMAKER LEAD TIP HEATING IN ABANDONED AND PACEMAKER-ATTACHED LEADS AT 1.5 TESLA MRI, published in the Journal of Magnetic Resonance Imaging 33:426-431 (2011).

Accordingly, what is needed is a low profile secondary header or adaptor that maintains close and compact apposition to the implantable medical device or pulse generator housing and/or its header and at the same time, disconnects the malfunctioning lead components from the pulse generator circuitry. The abandoned lead conductor(s) and its components should be connected to an MRI energy dissipating surface of the secondary header, and the secondary header should closely conform to the implantable medical device so as to minimize the in-growth of any intervening fibrous scar or mesothelial tissue.

There is also a need for a low profile secondary header or adaptor that conforms to the immediately adjacent and apposed therapy delivery apparatus, provide a receptor connector cavity allowing for insertion of the partially failed DF4 or IS4 (or equivalent) lead connector and thereby continued use of the selected, still functional components of a multifunctional implantable medical device lead, injector catheter or other chronically implantable, partially multifunctioning therapy delivery device. Such a compact, secondary header is needed which may provide one or more additional connector cavities wired for the functions disconnected from the DF4 or IS4 lead for insertion of the connectors of a new or reused lead or leads. Further, such a device is needed which allows continued use of an implanted lead, such as a DF4 or IS4 lead, which has partially failed, so as to eliminate the necessity for entirely replacing the failed lead, while simultaneously allowing the implantation of a supplemental lead to correct for the original leads failure.

The present invention fulfills these needs and provides other related advantages.

SUMMARY OF THE INVENTION

The present invention relates to a low profile secondary header for an active implantable medical device (AIMD), incorporating a connector cavity having a plurality of electrical contacts. The secondary header comprises (1) a secondary header plug configured for mating physical and electrical insertion into the AIMD connector cavity, (2) a secondary header cavity disposed within a housing and having at least one electrical contact conductively coupled to a respective at least one electrical contact on the secondary header plug, and (3) an intermediate conformal section between the secondary header plug and the secondary header connector cavity housing, for placing the secondary header connector cavity housing adjacent to an exterior surface of the AIMD when the secondary header plug is placed within the AIMD connector cavity.

Preferably, the secondary header connector cavity housing is spaced no more than 2 mm from the AIMD exterior surface, and most preferably the secondary header connector cavity housing has an exterior surface which tightly conforms to the adjacent AIMD exterior surface.

The secondary header may further or alternatively comprise (1) a secondary header plug configured for mating physical and electrical insertion into the AIMD connector cavity, the secondary header plug having a plurality of electrical contacts which correspond to the plurality of electrical contacts of the AIMD connector cavity, and (2) a secondary header connector cavity having the same physical dimensions as the AIMD connector cavity, and one or more electrical contacts, but less than the number of secondary header plug electrical contacts, conductively coupled to respective secondary header plug electrical contacts. At least one replacement lead connector cavity is further provided having at least one electrical contact conductively coupled to at least one secondary header plug electrical contact.

In a preferred form of the invention, a secondary header for an active implantable medical device (AIMD) incorporating an ISO DF4 or IS4 connector cavity having four electrical contacts is provided. As used herein, the ISO standard refers to American National Standard ANSI/AAMI/ISO 27186:2010, entitled, "Active Implantable Medical Devices—4-Pole Connector System for Implantable Cardiac Rhythm Management Devices—Dimensional and Test Requirements". The secondary header comprises (1) a secondary header plug configured for mating physical and electrical insertion into the AIMD ISO DF4 or IS4 connector cavity, the secondary header plug having four electrical contacts which correspond to the four electrical contacts of the AIMD ISO DF4 or IS4 connector cavity, (2) a secondary header ISO DF4 or IS4 connector cavity having less than four electrical contacts conductively coupled to the secondary header plug electrical contacts, and (3) at least one replacement lead connector cavity having at least one electrical contact conductively coupled to at least one electrical contact of the secondary header plug.

In this embodiment, at least one replacement lead connector cavity incorporates an ISO IS-1 and/or DF-1 connector cavity. The secondary header auxiliary plug may be configured for mating physical and electrical insertion into an AIMD ISO IS-1 or DF-1 connector cavity, and a passthrough lead connector cavity having at least one electrical contact conductively coupled to at least one electrical contact on the secondary header auxiliary plug.

In a preferred embodiment, an energy dissipating surface is electrically connected to one or more electrical contacts of the secondary header connector cavity which are not conductively coupled to the secondary header plug electrical contact. The energy dissipating surface may disposed on an exterior surface of a housing for the secondary header connector cavity, and may substantially encircle at least a portion of the secondary header connector cavity housing. Alternatively, the energy dissipating surface may be disposed in a recess formed on the exterior surface of the secondary header connector cavity housing.

A diverter circuit is electrically connected between the energy dissipating surface and the one or more electrical contacts of the secondary header connector cavity which are not conductively coupled to the secondary header plug electrical contacts. The diverter circuit may comprise a short, a capacitor, an R-C circuit, an L-C trap, or an R-L-C circuit.

Further, an RFID tag may be affixed or embedded within the secondary header.

In another embodiment, the secondary header ISO DF-4 or IS4 connector cavity has no electrical contacts conductively coupled to any electrical contact on the secondary header plug.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
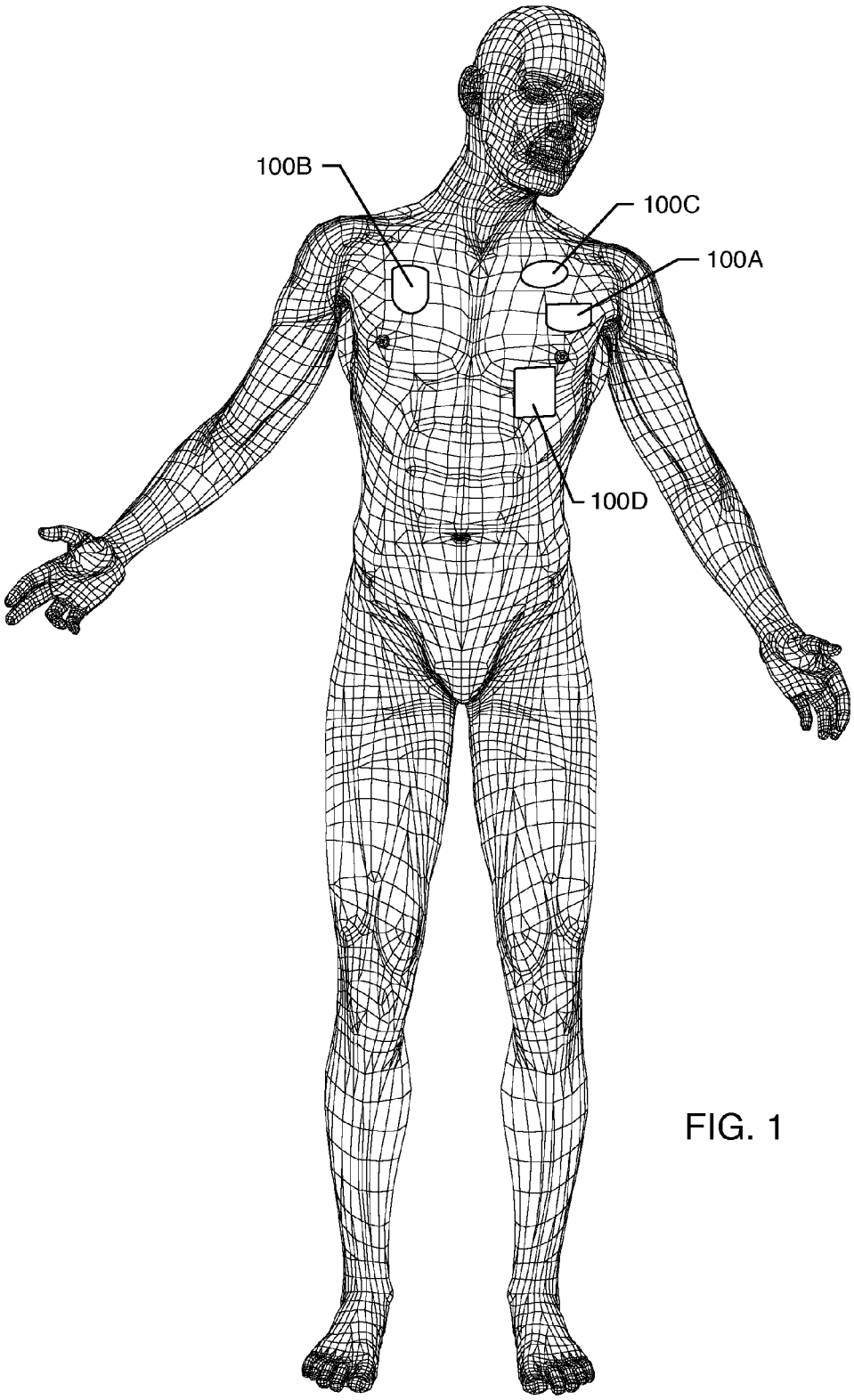
FIG. 1 illustrates a wire form drawing of a human body showing various active implantable medical devices (AIMDs)

The present invention is directed to a secondary header for use with implantable medical devices. More particularly, the secondary header of the present invention is intended to replace or supplement dysfunctional or inactive conductors or connections in medical leads.

Reference is made to section 3 of ISO Standard 27186 as providing definitions to terms and terminology which are used to describe the present invention. Accordingly, as used herein: "bipolar" means having two poles or electrodes; "connector system" refers to an assembly consisting of a lead connector and a connector cavity that are electrically and mechanically joined; "connector cavity" is defined as a cavity within the pulse generator which is intended to receive a lead connector and an identical cavity within a secondary header; "fixation zone" is a zone located in the lead connector pin and within the connector cavity where the lead connector is mechanically secured within the connector cavity; "high-voltage" is defined as electrical potentials greater than 20 volts up to 1000 volts (Note: High-voltages are generally used for defibrillating the heart); "lead connector" or "plug" is the part of the lead that is intended for insertion into the connector cavity of a pulse generator; "lead connector contacts" are defined as conductive elements on the lead connector which include the lead connector pin and lead connector rings; "lead connector pin" is defined as the most proximal conductive element of a lead connector provided for making electrical contact as well as for securing the lead connector within the connector cavity; "lead connector ring"defines angular conductive elements on the lead connector intended for making electrical contact within the connector cavity (Note: the 4-pole connector (DF4 or IS4) has up to 3 lead connector rings and a lead connector pin); "lead electrode" is the distal part of a lead through which electrical impulses are transmitted to or from cardiac tissue (Note: high-voltage electrodes are capable of delivering high-voltage electrical impulses; Low-voltage electrodes are used for transmitting and sensing low-voltage impulses and are generally not suitable for delivering high-voltage); "low-voltage" defines electrical potentials less than or equal to 20 volts; "pulse generator" is any type of active implantable medical device (AIMD) and particularly those devices that deliver electrical energy to effect cardiac rhythms; "securing mechanism" is defined as a mechanism within the connector cavity intended for mechanically securing the lead connector (Note: a securing mechanism can be an active mechanism, such as a set screw or it can be a passive mechanism, such as a self-engaging latch; It can also serve a second function of providing electrical contact with the lead connector, as is the case with a set screw); "tripolar"means having three poles or electrodes.

Furthermore, as used herein the term "lead" refers to an implantable lead which has a lead body and one or more conductors. "Lead conductor" refers to one or more coiled or filer wires which are located within the lead body. Lead conductors are generally insulated from each other. The term "leadwire" refers to internal wires or circuit traces within the secondary header of the present invention. Leadwires may also refer to wires or circuit traces that are located entirely inside of the AIMD hermetically sealed housing.

The present invention allows one to safely reactivate and repair a DF4 and/or an IS4 lead having one or more failed conductor components or functions. After unplugging the connector of the malfunctioning lead from the connector cavity of the associated pulse generator, ICD or resynchronization pulse generator, the novel secondary header of the present invention is then plugged into the DF4 or IS4 connector cavity of the AIMD. The previously implanted multiconductor and multifunction lead with its one or more failed conductors or components, is then plugged into the DF4 or IS4 connector cavity of the secondary header. The proper secondary header is selected so that after insertion, the defective or non-therapeutically optimal lead function is (or functions are) disconnected from the AIMD electronic circuits. A secondary connector cavity in the secondary header, which may be either IS-1 or DF-1 depending on the original leads suffering component failure, contains the electrode contacts redirected from the primary connector cavity for the partially defective DF4 or IS4 lead. The repair may then be completed by implanting a new IS-1 or DF-1 lead, depending on the failed function, and plugging the new lead into the secondary header connector cavity. Implanting one of these smaller diameter leads puts less burden on the venous system and the tricuspid valve than if the original DF4 lead was simply abandoned and a second parallel generally much larger diameter DF4 lead was placed into the venous system and right side of the heart, In a preferred embodiment, the new secondary header embodies a low profile design different than any prior art lead adaptor and fits compactly against the associated pulse generator so that tissue pocket bulk is minimized and little or no extra dissection is required at subsequent surgery. Setscrews are to be minimized or eliminated, by utilizing approved IS-1 and DF4 spring and ring contacts, so that the use of notoriously poor sealing standard header grommets can be avoided. However, a single setscrew for pin retention and electrical contact may be included if required to be in compliance with ISO Standards.

Accordingly, the present invention is directed towards correction of essentially all DF4 or IS4 lead conductor component failures or dysfunctions occurring at any time post initial implant, including low voltage pace-sense failures. The present invention provides a hard-wired secondary header that disconnects the one or more defective lead components from AIMD electronics and provides additional connector cavities where smaller diameter lead connectors can be inserted to replace any and all defects. In addition, the present invention provides that the existing DF4 (or IS4) lead can be reinserted into an inlet or a secondary header connector cavity so that its functional conductor components can still be utilized. In a preferred embodiment, energy dissipating surfaces are connected to the abandoned lead conductor components thereby significantly reducing the risk to the patient that the abandoned lead conductor(s) would overheat and cause damage to adjoining tissues during an MRI procedure. In a further preferred embodiment, the novel secondary header contains an RFID chip and antenna providing at a minimum the date of manufacture of the secondary header, its model and serial number, and the specific subtype of failure and repair it was designed to address.

FIG. 1 is a wire form diagram of the human body showing various active implantable medical devices. 100A is a cardiac pacemaker. 100B illustrates an implantable cardioverter defibrillator (ICD). It should be noted that while the pacemaker 100A is shown in the region of a left pectoral pocket, and the ICD is shown in the right pectoral pocket area, in the art, either of these may be placed in either or other pockets. 100C indicates a general neurostimulator which could be a deep brain stimulator or it could be relocated to other positions in the body, such as a spinal cord stimulator and the like. Certain neurostimulators use ISO Standard connectors. Accordingly, the present low profile secondary header invention can apply to any type of neurostimulators. In fact, pacemakers and implantable defibrillators are a subset of the whole class of electrical neurostimulators and all may stimulate body tissue with electrical pulses or the like. 100D indicates an artificial heart or left ventricle assist device, some of which may also use ISO Standard connectors.

Figure 2:
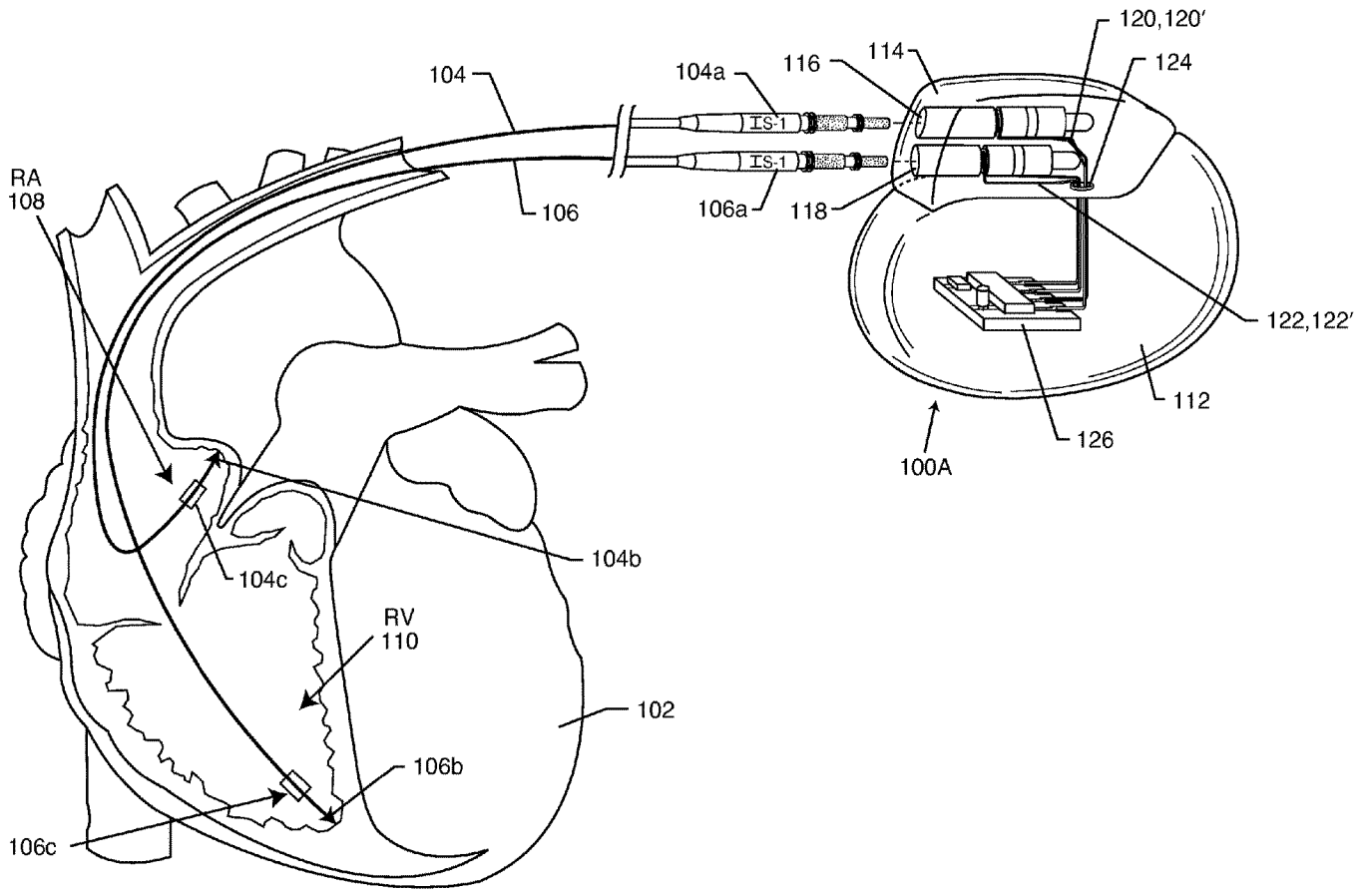
FIG. 2 PRIOR ART
FIG. 2 illustrates a prior art dual chamber bipolar pacemaker with leads implanted into a human heart.

FIG. 2 shows a prior art outline diagram of the human heart 102 and a cardiac pacemaker 100A. Shown are two implanted leads 104 and 106 which both have IS-1 connectors 104a, 106a at their proximal ends. Lead 104 is routed transvenously into the right atrium (RA) 108 of the heart 102. Lead 104 is a bipolar lead, meaning that it has two conductors. One of the lead conductors terminates in the distal tip electrode 104b and the other conductor terminates in the distal ring electrode 104c. Implanted lead 106 is routed into the right ventricular cavity (RV) 110. It is also bipolar, meaning that it has two conductors, one of which is connected to the distal tip electrode 106b and the other conductor is connected to the distal ring electrode 106c. This is known in the art as a dual chamber bipolar pacemaker 100A. The pacemaker 100A has a metallic housing 112 generally of titanium, stainless steel or the like. It also has a header block 114 which holds connector assembly components in accordance with ISO Standard IS-1. In this case, the header 114 has two connector cavities 116 and 118 into which the IS-1 lead proximal connectors 104a, 106a can be inserted. Generally, there would be set screws to fix the connector ring and pin electrodes firmly in place (not shown). There are leadwires 120, 120', 122, 122' routed from the connector cavities 116, 118. These four leadwires 120, 120', 122, 122' are routed to a hermetic seal 124 where the wires pass through the housing 112 in non-conductive relation. It is very important that the housing 112 of the AIMD be completely hermetic to protect sensitive electronic components, for example, those that are shown on circuit board 126.

Figure 3:
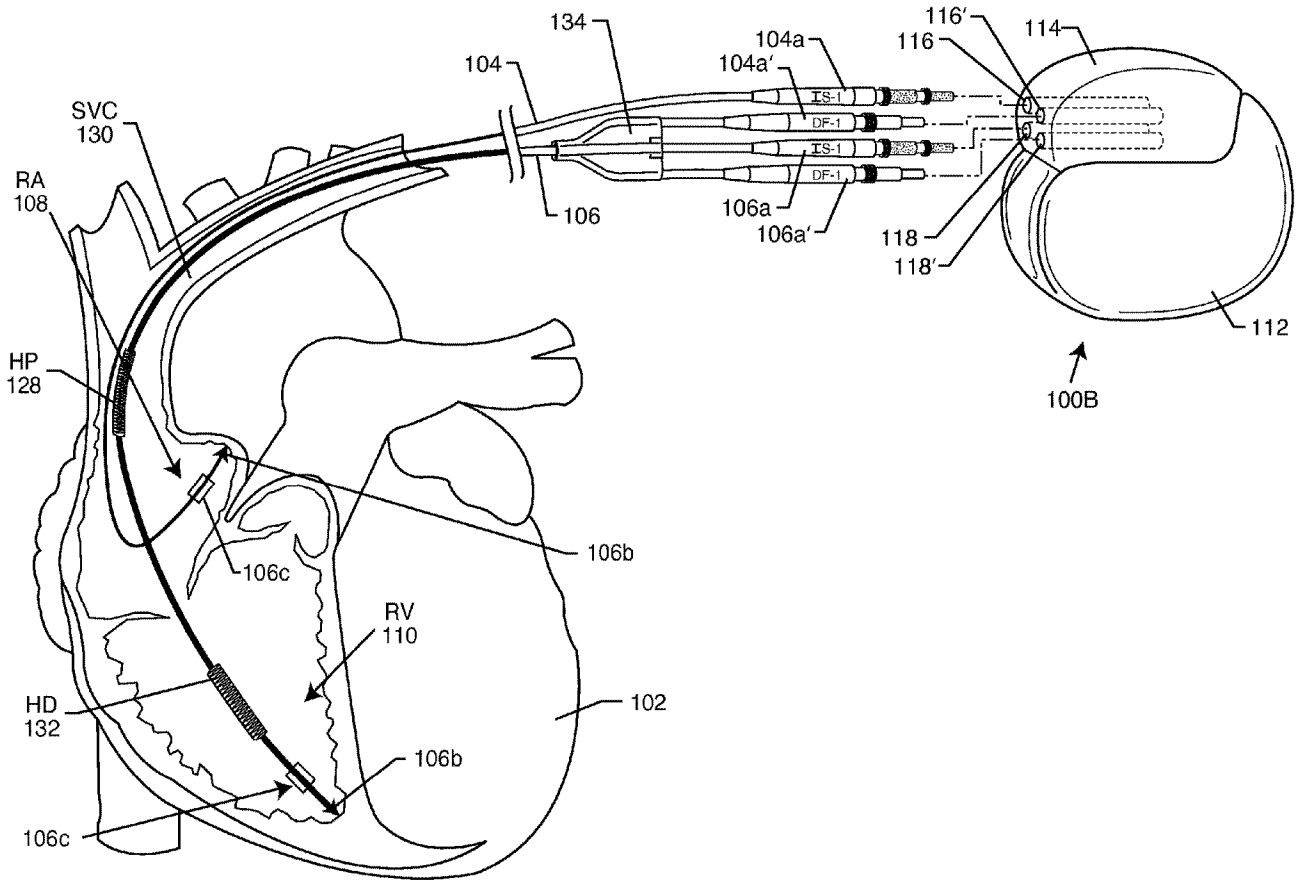
FIG. 3 PRIOR ART
FIG. 3 illustrates a prior art dual chamber implantable cardioverter defibrillator with leads and shocking coils implanted into a human heart. Note the complex trifurcated connector on the quadripolar ventricular lead.

FIG. 3 also shows a prior art outline drawing of a human heart 102 and in this case, the device 100B is a dual chamber implantable cardioverter defibrillator. One can see that there are four connector cavities 116, 116', 118, 118' into which the IS-1, DF-1, IS-1 and DF-1 proximal connectors 104a, 104a', 106a, 106a' may be inserted. Again, there are two implanted leads 104 and 106. Bipolar lead 104 is transvenously inserted into the right atrium 108 of the heart 102. It has a distal tip electrode 104b and a distal ring electrode 104c. Lead 106 has four conductors. Two of these conductors route to the distal tip electrode 106b and the distal ring electrode 106c. The DF-1 connectors 104a', 106a' are high-voltage conductors. One of the high-voltage connectors 104a' is routed to shocking coil (HP) 128, which is generally located in the superior vena cava (SVC) 130 of the heart 102. The second high-voltage shocking coil (HD) 132 is located in the right ventricle 110. In total, there are 6 lead conductors in the system, as shown in FIG. 3.

In FIG. 3, one can see that there is a trifurcated lead adaptor 134 which combines the connectors 104a', 106a, 106a' for the two high-voltage shocking coils 128, 132 along with one low-voltage tip 106b and ring 106c circuit. In the prior art, excess lead is typically wound up in the pectoral pocket, either adjacent to or around the pacemaker. The trifurcated adaptor 134 and lead system 104, 106, as shown in FIG. 3, makes for a very bulky pectoral pocket lead arrangement as compared to the arrangement shown in FIG. 2. In addition the four separate connectors and associated proximal lead segments tend to create crisscrossing tissue ingrowth paths. When the ICD 100B needs to be replaced for approaching battery end of life or any other indication, this tangle of insulated conductor segments all tend to have tissue in-growth which makes the surgery difficult as all of these leads must be carefully excised and separated.

Figure 4:
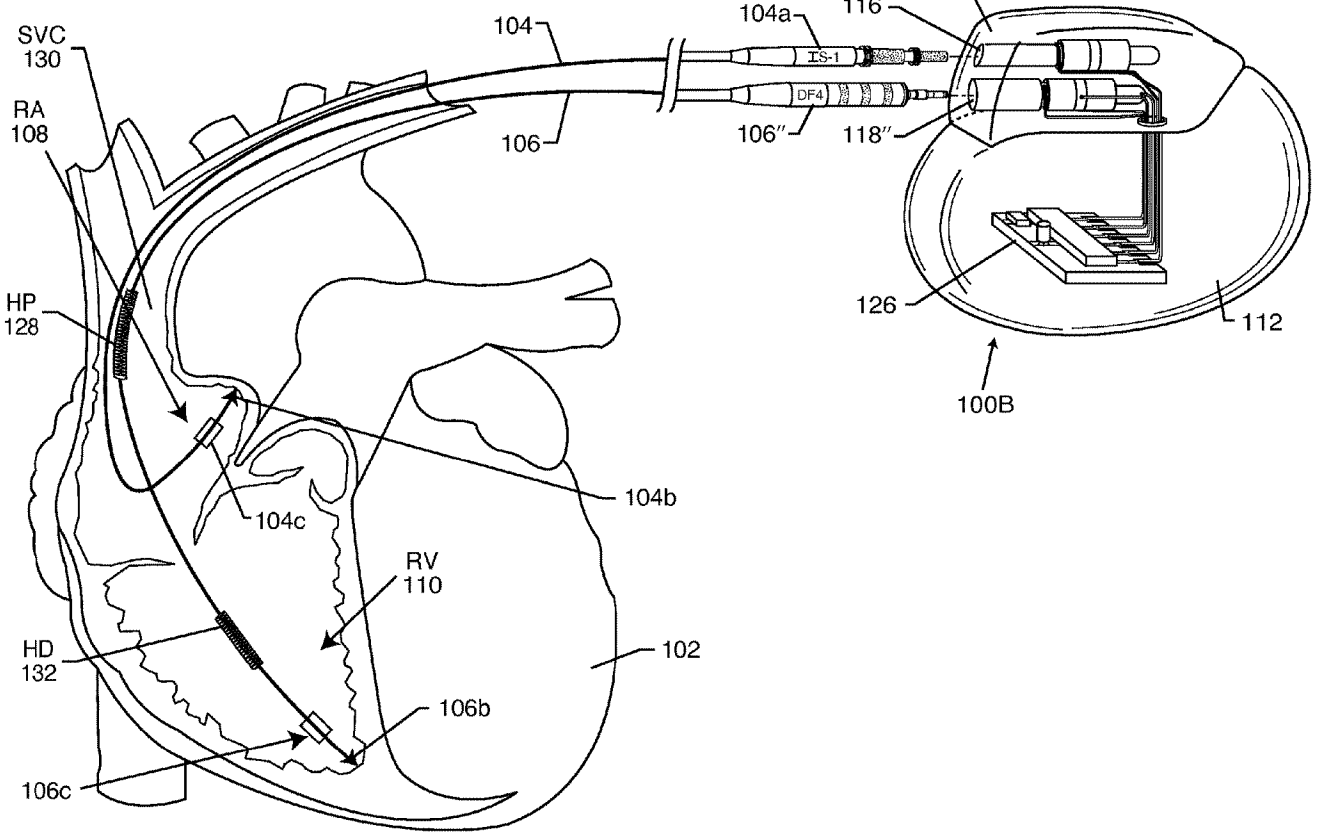
FIG. 4 PRIOR ART
FIG. 4 illustrates a state-of-the-art dual chamber implantable defibrillator similar to FIG. 3 but with the new in-line DF4 quadripolar connector replacing the prior cumbersome trifurcated lead based adaptor.

FIG. 4 is another prior art cross-section of the human heart 102 again with a dual chamber ICD 100B. As illustrated in FIG. 3, the dual chamber ICD 100B has both pacing and high-voltage shocking functions. The electrode placements, both for the high-voltage shocking coils and also the low voltage pace and sense circuits are the same as previously described for FIG. 3. However, in FIG. 4, the defibrillator 100B lead 106 incorporates the new state-of-the-art inline quadripolar DF4 proximal lead connector 106a" as shown. In this case, there are now only two connector cavities 116 and 118" in the defibrillator 100B header 114. Connector cavity 116 is a low-voltage connector cavity for receipt of the IS-1 proximal connector 104a. Connector cavity 118" is a DF4 quadripolar connector cavity designed to receive the DF4 proximal connector 106a". In this case, there are still two leads 104 and 106 that are routed down into the various chambers of the heart as previously described in FIG. 3. When one considers that excess lead is wound up in the pacemaker pocket, one can see that the configuration in FIG. 4 is vastly superior to the trifurcated connector 134 as previously illustrated in FIG. 3. The surgical implant procedure is considerably simplified and there is a lot less bulk created in the pacemaker pocket which increases both reliability and patient comfort.

Figure 5:
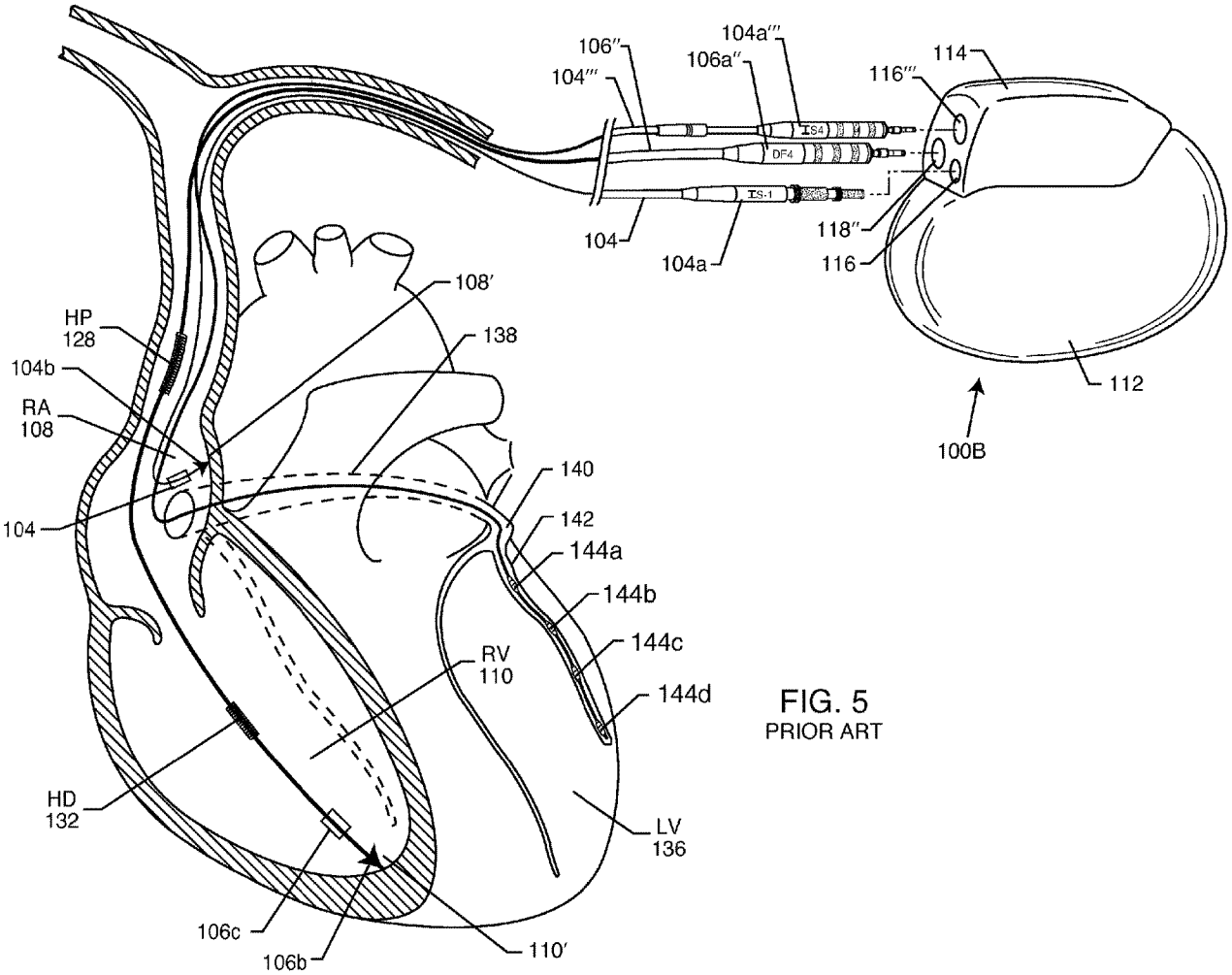
FIG. 5 PRIOR ART
FIG. 5 illustrates a prior art dual chambered ICD that also employs a quadripolar left ventricular lead for simultaneous stimulation of the right and left ventricles, so called cardiac resynchronization therapy or CRT. Thus this system has both DF4 and IS4 quadripolar leads, including in-line connectors for insertion into corresponding DF4 and IS4 connector cavities.

FIG. 5 is a prior art drawing of a human heart 102 and ICD 100B that is state-of-the-art. This defibrillator system not only has high-voltage shocking and low-voltage pacing functions, but it also has cardiac resynchronization therapy (CRT) capabilities through electrodes placed transvenously into the right atrium 108 and then through the coronary sinus 138 into epicardial veins 140, 142 on the surface of the left ventricle (LV) 136. In this case, there are two types of quadripolar connectors being used at the proximal lead ends. There are three implanted leads 104, 104''' and 106". Lead 104 is a low-voltage lead which is routed to distal tip 104b and ring 104c electrodes in the right atrial appendage 108'. Lead 106" is a quadripolar low-voltage/high-voltage lead. Lead 106" contains four conductors, two of which are connected to high-voltage shocking coils 128 and 132. There are also two low-voltage conductors in lead 106" which are routed to the distal tip electrode 106b and distal ring electrode 106c in the right ventricular apex 110'. The third lead 104a is a four-conductor IS4 or quadripolar lead which is routed transvenously through the coronary sinus 138, the great cardiac vein 140 and into a branch vessel 142 which is part of the epicardial or surface venous system draining blood from the left ventricle 136 back into the right atrium 108. Shown are four electrodes 144a through 144d. The IS4 proximal connector for lead 104''' is plugged into connector cavity 116''' on the header block 114 of the ICD 100B. The DF4 connector 106" is plugged into connector cavity 118" and the IS-1 proximal connector 104 is plugged into connector cavity 116 as shown.

Referring once again to FIGS. 4 and 5, it is obvious that the use of inline quadripolar connectors greatly reduces the number of required connectors. As previously mentioned, there are a number of major advantages associated with this in addition to less bulk in the device tissue pocket. However, there is no provision in the DF4 or IS4 Standards for what remedial steps to take if one of the lead conductors or other components fails or becomes inoperable or is dysfunctional. For those experienced in the implantable medical device business, they realize that the implanted lead is almost always the weak point in the system. In other words, it is not uncommon for lead conductors, insulation, and fixation mechanisms to fail in a variety of ways. Since 1980, there have been a continual series of lead recalls, including the 2007 recall of all the Medtronic Sprint Fidelis models, and the more recent recall of some St. Jude's ICD lead models. Average failure rates of some quadripolar ICD lead models, approaching 25% after implantation in female patients for 5 years, and of over 15% in male patients, have been independently documented in a recent multi-center publication in the leading journal Circulation. And failure rates were even higher if the popular subclavian or particularly an axillary vein access route was chosen. These recalls are not only financially damaging for the industry and the companies involved, but are also devastating for the patients who have to go through additional surgeries to replace defective leads. In addition they place great stress on healthcare delivery systems, physicians, and hospital and clinic staff members etc. In short, as time goes on and the DF4 and IS4 quadripolar connector leads become more popular, it is unavoidable that some degree of lead conductor or component failures or dysfunction requiring repair will occur. While it is hoped that these failures will be at a much lower rate than in the recent recalls, there is no guarantee, as independent reports comparing the ICD lead products of the major manufacturers indicate a minimum failure rate of even less complex tripolar products in the range of 8 to 10% by 10 years (Circ Arrhythmia Electrophysiol. 2009; 2:411-416). It is still important therefore to consider what will happen when a patient is presented with a DF4 or IS4 lead failure or malfunction. Referring to FIG. 5, for example, let's say there was a failure in the DF4 lead 106" wherein, there was a defect in the conductor or electrode 106b, 106c. This could mean that there was a fracture in the lead conductor or that the distal electrode 106b became dislodged or even that there was an increase in what's known as pacing capture threshold (PCT) or an insulation breach. In any event, loss of proper pacing and/or biologic signal sensing capabilities involving electrode 106b can cause a catastrophic clinical outcome for a patient depending on the system as shown in FIG. 5. In fact, if the patient was continuously pacemaker dependent, the loss of pacing function would be immediately life-threatening. If the physician is presented with such a case wherein for example, one of the four conductors in lead 106" has failed, there are currently no good choices. Explanting lead 106" will be difficult since tissue in-growth tends to tie all three leads together. Even using a laser sheath to try to vaporize the non calcified adhesions is not always successful, involves risks to the patient and to the maintenance of position and function of the still functional 104 and 104'" leads. One choice would be to remove the defibrillator 100B and replace it with a special four-connector cavity defibrillator. In this case, an additional low-voltage connector cavity would be provided so that an additional low-voltage lead could be implanted into the right ventricle. The low-voltage tip electrode 106b and ring electrode 106c and their associated lead conductors would be abandoned and left in place. A new low-voltage lead would be transvenously inserted down into the right ventricle 110 into a location that provided for proper pacing capture and sensing. Thus, the patient would gain an additional relatively small diameter lead which typically would not present any major physiologic problems. While this presents a way to implant an extra lead to make up for the failed conductor or component in lead 106", it comes at great expense (at least $20,000 for the replacement custom header defibrillator) plus the waste of the standard ICD that has to be explanted and discarded.

Figure 6:
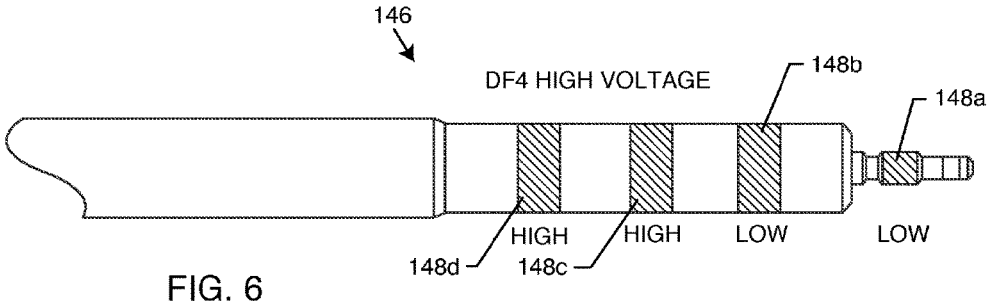
FIG. 6 PRIOR ART
FIG. 6 is an enlarged view of the proximal lead connector for the new DF4 high-voltage lead.

FIG. 6 is an enlarged pictorial view of an embodiment of a proximal end portion of a DF4 high-voltage connector 146. As can be seen, at its proximal tip, it has a low-voltage pin electrode connection contact 148a and it also has a ring low-voltage connection 148b next in line. In addition, it has two high-voltage ring connection contacts 148c and 148d. This makes for a four-conductor lead as previously described as lead 106a" in FIGS. 4 and 5. This is the same as the DF4 lead 106" previously shown in FIG. 5.

Figure 7:
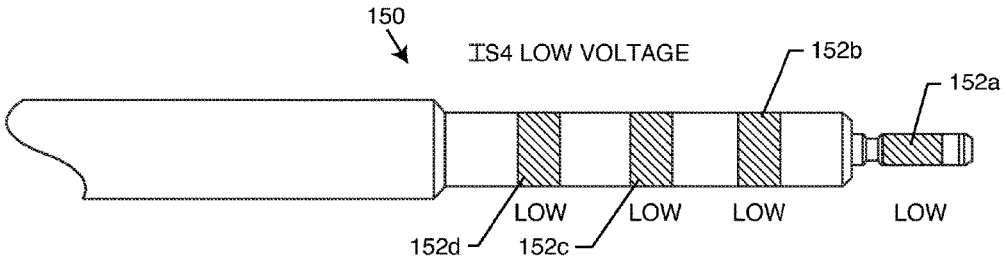
FIG. 7 PRIOR ART
FIG. 7 is an enlarged view of the new IS4 low-voltage lead connector.

FIG. 7 is a blown-up pictorial view of an embodiment of a proximal end portion of a IS4 low-voltage quadripolar lead connector 150. As illustrated, the connector 150 comprises a low-voltage connector tip 152a and three low-voltage electrode connection contacts 152b, 152c and 152d. This is the same as the low-voltage IS4 left ventricular lead 104'" as previously described in FIG. 5.

Figure 8A:
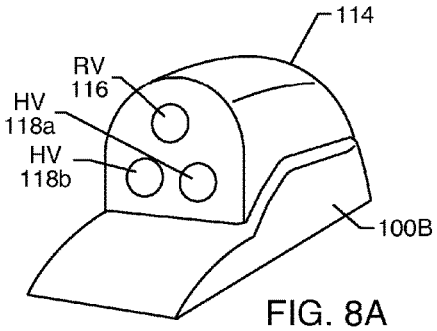
FIG. 8A PRIOR ART
FIG. 8A illustrates the header block of a prior art implantable single chamber defibrillator showing two high-voltage DF-1 connector cavities and a single low-voltage IS-1 connector cavity.

FIG. 8A illustrates a prior art header connector block 114 of an AIMD 100B with two high-voltage (HV) connector cavities 118a, 118b which are both DF-1 and a low-voltage (RV) bipolar connector cavity 116 in accordance with IS-1. Each high-voltage connector cavity 118a, 118b would be unipolar and routed to a defibrillation shock coil 128, 132. The low-voltage connector cavity 116 would be bipolar and routed to a distal tip 104b and ring 104c electrode.

Figure 8B:
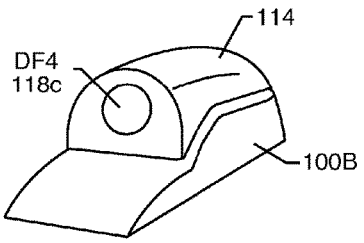
FIG. 8B PRIOR ART
FIG. 8B illustrates how the new quadripolar DF4 connector provides equivalent function to FIG. 8A but with one rather than three primary header connector cavities.

FIG. 8B is exactly the same system illustrated in FIG. 8A except that the three connector cavities have been replaced with a single DF4 quadripolar connector or cavity 118c. In this case, both the high-voltage and the low-voltage functions are all in one DF4 connector 146 as previously illustrated in FIG. 6.

Figure 9A:
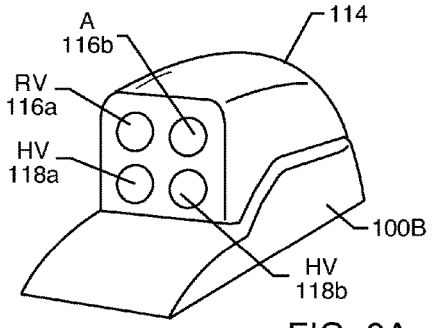
FIG. 9A PRIOR ART
FIG. 9A illustrates a dual chamber defibrillator header with both atrial and ventricle connector cavities. The high-voltage connector cavities are DF-1 and the right ventricular and atrial connector cavities are IS-1.

FIG. 9A is the header 114 of a dual chamber defibrillator 100B with DF-1 high-voltage (HV) connector cavities 118a, 118b for attachment of high voltage coil electrode leads for delivery to the RV 110 and an alternate site, usually in the superior vena cava 130. In addition, there are two low-voltage connector cavities (RV) 116a, (A) 116b. One for a lead to be routed to the right ventricle 110 and the other to the right atrium 108. In this case, there would be two DF-1 connectors and two IS-1 connectors at the proximal ends of the required leads.

Figure 9B:
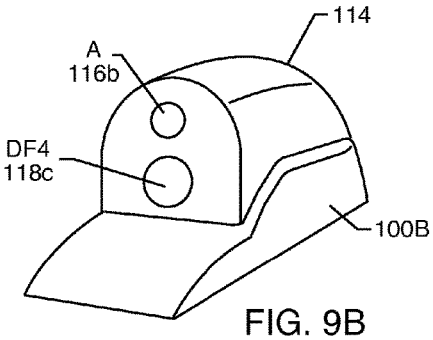
FIG. 9B PRIOR ART
FIG. 9B is the state-of-the-art equivalent to FIG. 9A wherein, both HV connector cavities and the RV IS-1 connector cavity have been replaced by a single inline DF4 quadripolar connector.

FIG. 9B shows how the inline quadripolar DF4 connector 146 can be used to reduce four connector cavities 118a, 118b, 116a and 116b to two cavities 118c and 116b. This is a logical progression from what is described in FIGS. 8A and 8B. One connector cavity 118c would be DF4 for streamlined provision of both low voltage ventricular pacing and sensing, and in addition dual coil high defibrillator function. The second connector cavity 116b, would be IS-1 bipolar capable of providing atrial electrical stimulation and sensing.

Figure 10A:
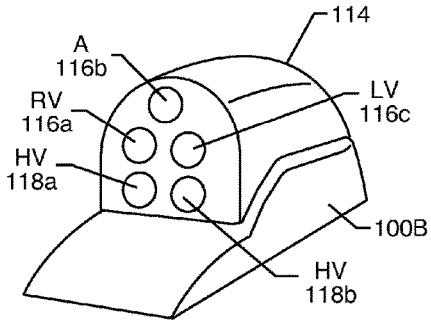
FIG. 10A PRIOR ART
FIG. 10A illustrates a dual chamber defibrillator with CRT capability.

FIG. 10A shows a dual chamber defibrillator 100B primary header 114 with the addition of CRT functions requiring a total of five connector cavities. The two high-voltage (HV) connector cavities 118a, 118b are DF-1 and the low voltage connector cavities (RV) 116a, (A) 116b and (LV) 116c are IS-1 connectors. Required leads and intended functions are identical to what is described in detail above. The additional, fifth low-voltage connector cavity is for receipt of an IS-1 type connector, whereby, a fifth lead would be routed through the venous system into the right atrium 108, the coronary sinus 138 and from there into subepicardial branch coronary veins near the lateral surface of the left ventricle, (see LV 136 in FIG. 5).

Figure 10B:
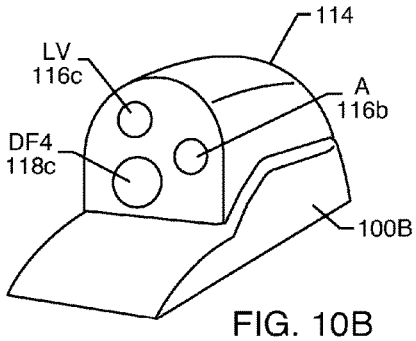
FIG. 10B PRIOR ART
FIG. 10B is the modern equivalent of FIG. 10A showing a DF4 quadripolar connector that replaces the 2 HV connector cavities and the RV IS-1 connector cavity in FIG. 10A.

FIG. 10B shows the system of 10A simplified from five to three connector cavities. The DF4 cavity 118c provides for combined dual coil high-voltage functions and the low voltage RV bipolar pace sense function, all into the newly standardized quadripolar connector. There is still a necessity to have a low-voltage connector cavity 116c for an IS-1 lead to be routed to the left ventricle and also an atrial connector cavity 116b as shown.

Figure 11:
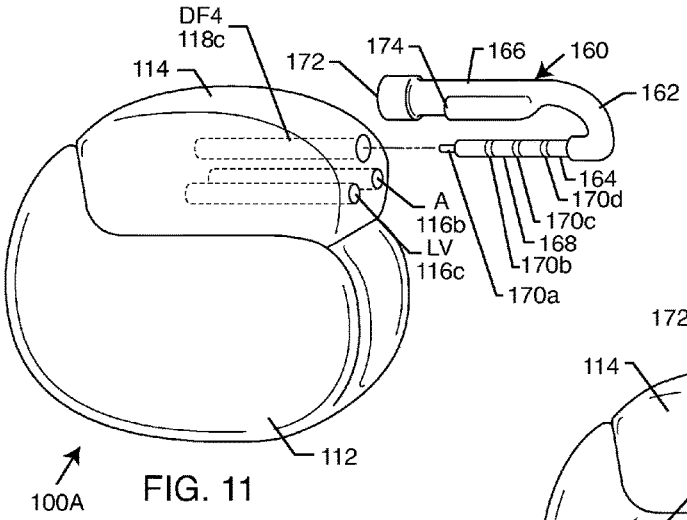
FIG. 11 illustrates an AIMD with a DF4 connector cavity, including a low profile conforming quadripolar secondary header of the present invention.

FIG. 11 illustrates a low profile secondary header 160 embodying the present invention. The body 162 of the secondary header 160 has a DF4 standard quadripolar connector 168 at the proximal end 164. It is designed to be inserted into the DF4 connector cavity 118c of the AIMD 100A. There are also left ventricle 116c and atrial 116b connector cavities. These leads are not shown for simplicity. One can see that the distal end 166 has a connector cavity 172 and also a replacement connector cavity 174. Connector cavity 172 is designed to receive the DF4 proximal connector from the previously quadripolar (or similar IS4) compatible implanted lead that has a defective conductor or other component (not shown). Replacement connector cavity 174 generally is in accordance with either the older ISO DF-1 or IS-1 Standards and is designed to receive the proximal connector of a new lead to be inserted by the physician to replace the failed DF4 function.

Figure 12:
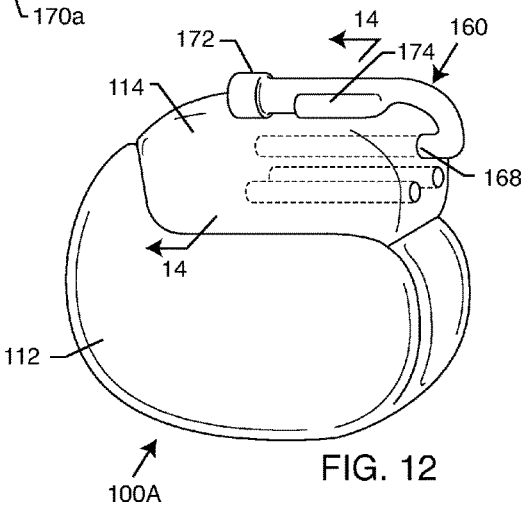
FIG. 12 illustrates the low profile secondary header shown inserted into the AIMD DF4 connector cavity.

FIG. 12 shows the low profile secondary header 160 of FIG. 11 inserted fully into the DF4 connector cavity 118c of the AIMD header block 114. As can be seen, the low profile secondary header 160 conforms and fits tightly against the AIMD header block 114. This low profile and tight fit is very important for patient comfort so that the additional bulk of the pulse generator plus secondary header and leads in the pectoral or other tissue pocket is minimized.

Figure 13:
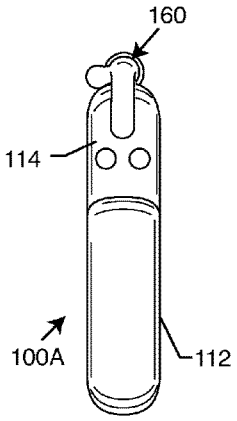
FIG. 13 illustrates an end view taken from FIG. 12.

FIG. 13 is an end view taken from FIG. 12 showing the low profile secondary header 160 conforming and fitting very tightly to the top of the AIMD 100A header connector block 114.

Figure 14:
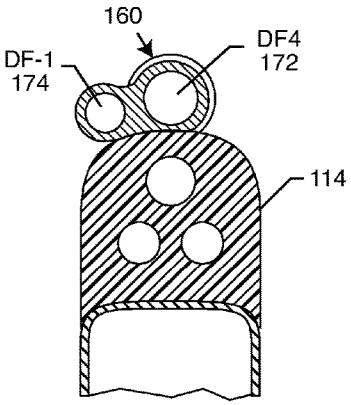
FIG. 14 illustrates a cross-sectional view taken from section 14-14 from FIG. 12.

FIG. 14 is a sectional view taken generally from section 14-14 from FIG. 13 showing the top of the AIMD 100A header 114 and a cross section of the low profile secondary header 160, including the interiors of the secondary header's, DF4 172 and in this case DF-1 174 connector cavities.

Figure 15:
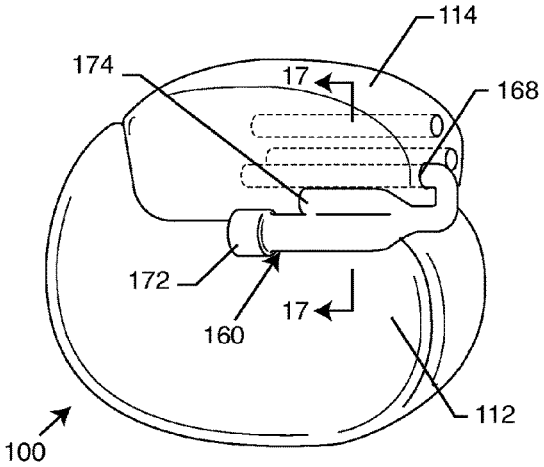
FIG. 15 shows the secondary header inserted into a different AIMD connector cavity and rotated along the side of the AIMD.

FIG. 15 shows the low profile secondary header 160 plugged into an alternate AIMD connector cavity location 168 and also rotated so that it fits alongside of the AIMD 100. In this case, the low profile secondary header 160 fits snugly against both the header 114 and the device housing 112.

Figure 16:
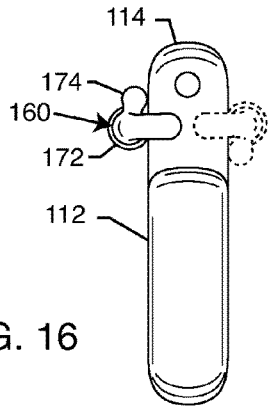
FIG. 16 illustrates an end view showing an alternate configuration for FIG. 15.

FIG. 16 is an end view taken from FIG. 15 showing that the connector cavities 172, 174 on the AIMD secondary header 160 can be reversed. FIG. 16 also illustrates that the low profile secondary header 160 can be rotated or clocked if inserted into another connector cavity, so that it can be on the left side as shown, or on the right side or on top as previously illustrated in FIG. 12.

Figure 17:
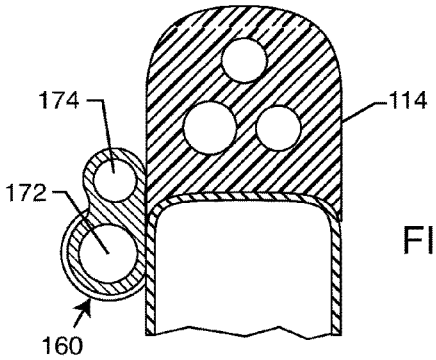
FIG. 17 is a cross-sectional view taken from section 17-17 from FIG. 15.

FIG. 17 is taken generally from section 17-17 from FIG. 15 showing the low profile secondary header 160 in sectional view. Connector cavity 172 conforms to either DF4 or IS4 and the replacement connector cavity 174 conforms to either IS-1 or DF-1. If the DF4 secondary header connector cavity 172 was instead on the lower right in this view, secondary header 160 would work equally as well but cavity 172 would be superior to cavity 174 with the two secondary header connector cavities 172, 174 straddling interface of the header 114 to AIMD housing 112.

Figure 18:
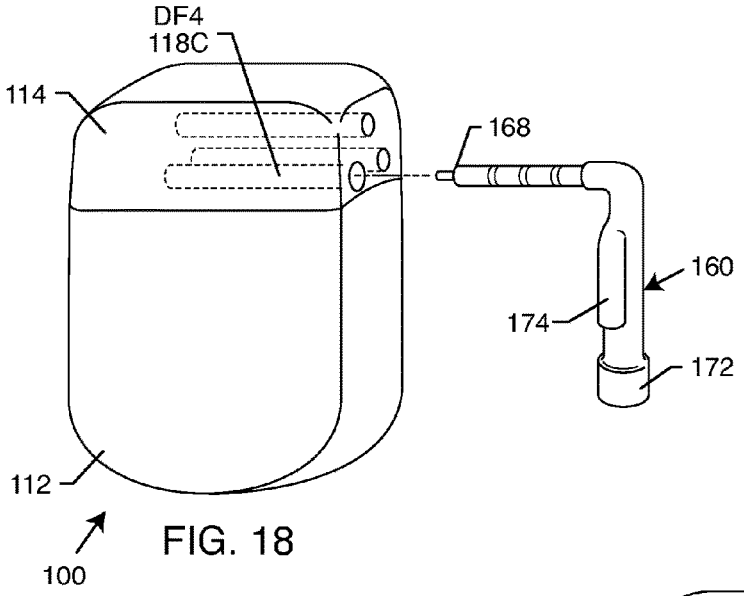
FIG. 18 shows an alternate shape of the low profile conforming secondary header.

FIG. 18 is an outline drawing of an active implantable medical device 100 which has a different shape than the devices as previously illustrated in FIGS. 11, 12 and 15. In this case, the low profile secondary header 160 has an L shape. Its connector plug 168 is designed to be inserted into the DF4 connector cavity 118c of the AIMD primary header 114.

Figure 19:
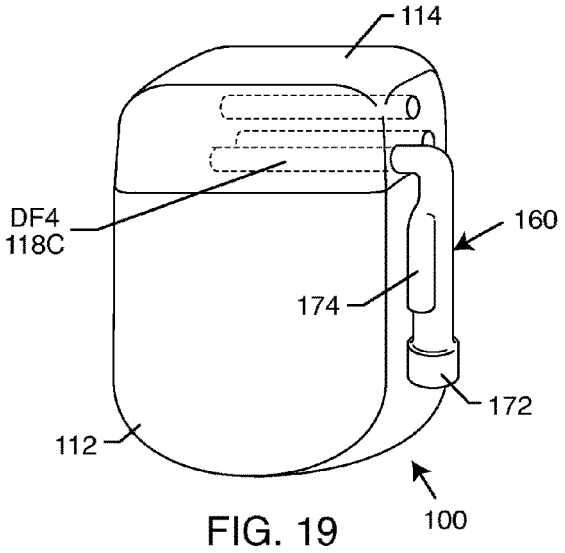
FIG. 19 shows the secondary header of FIG. 18 inserted into a connector cavity of the AIMD.

FIG. 19 shows the device of FIG. 18 with the low profile secondary header 160 plugged into cavity 118c where it fits tightly against the AIMD device housing 112.

Figure 20:
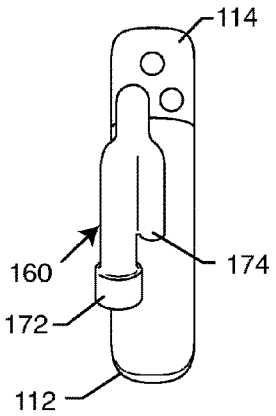
FIG. 20 is an end view that illustrates that the secondary header is plugged into a different AIMD connector cavity location.

FIG. 20 is an end view taken generally from FIG. 19. In this case, it is illustrated that the low profile secondary header 160 connector cavities 172 and 174 can be reversed.

Figure 21:
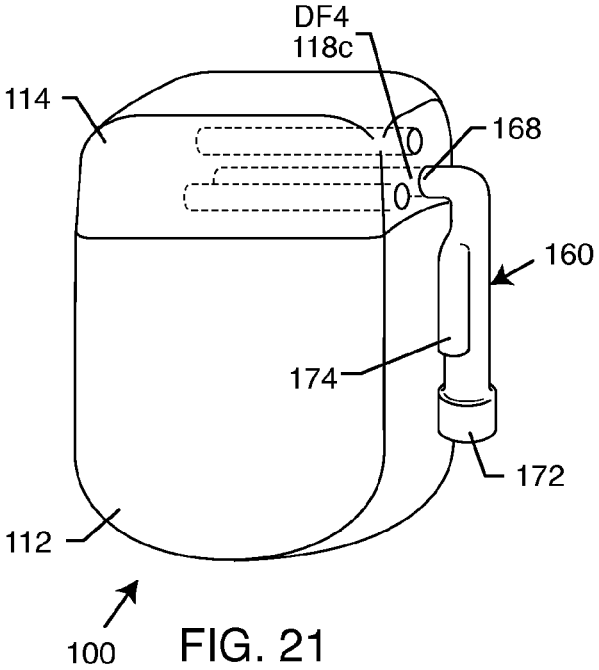
FIG. 21 illustrates an alternate form of the low profile secondary header.

FIG. 21 is very similar to FIG. 19 except that the low profile secondary header 160 has been plugged into the lower right hand connector cavity 118c of the AIMD 100 primary header 114.

Figure 22:
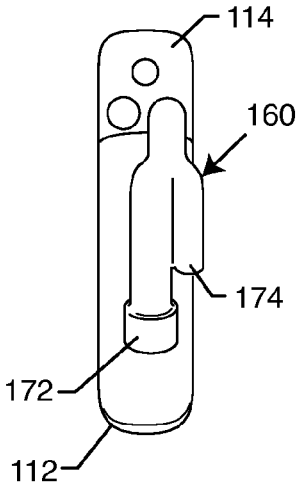
FIG. 22 illustrates an end view taken generally from FIG. 21 also showing an alternate configuration of the secondary header.

FIG. 22 is an end view taken from FIG. 21 illustrating that the low profile secondary header 160 and its connector cavities 172 and 174 conform and fit tightly to the AIMD 100 header 114 and housing 112. In this case, the AIMD 100 is a dual chamber, plus resynchronization cardioverter defibrillator as in FIG. 10B.

Figure 23:
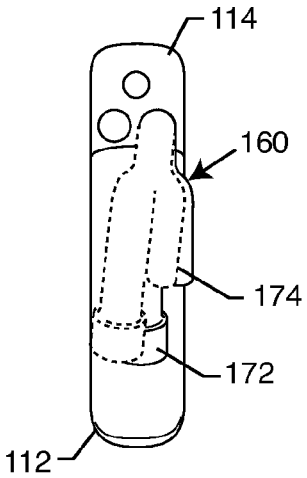
FIG. 23 shows how the secondary header of FIG. 22 can be rotated or clocked.

FIG. 23 is very similar to FIG. 22 showing that the low profile secondary header 160 can be rotated as shown, so as to minimize any projection beyond the edge profile of the pulse generator.

Figure 24:
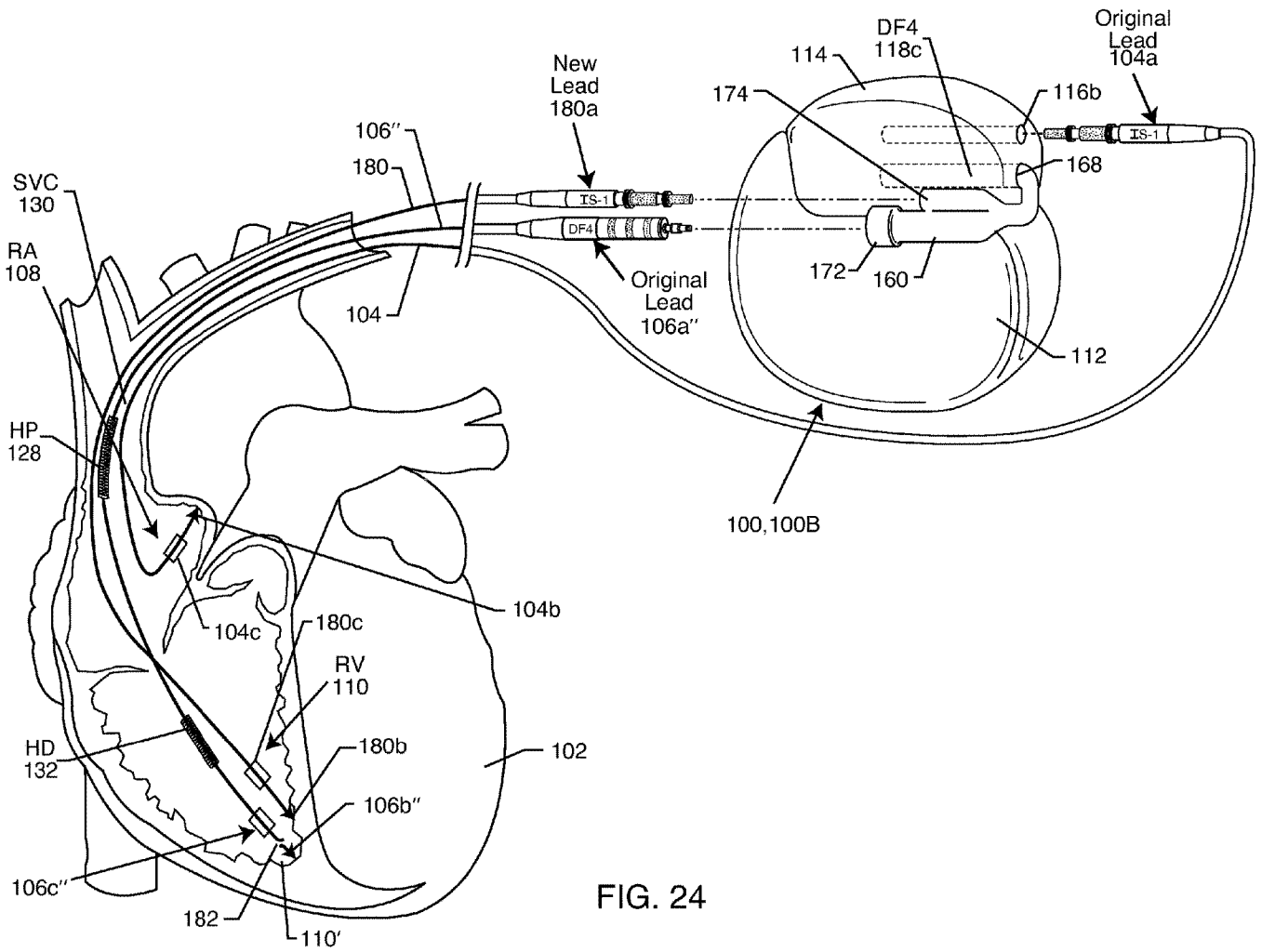
FIG. 24 illustrates a previously implanted lead system similar to FIG. 4 wherein, one of the DF4 low voltage conductors has failed. A low profile conforming secondary header of the present invention is illustrated along with the connectors of the partially failed DF4 lead and the connector of the new IS-1 lead implanted to replace the failed function.

FIG. 24 shows an AIMD 100,100B with lead connections into the outlined drawing of a human heart 102. FIG. 24 illustrates a DF4 compatible ICD and leads 106", 104 that had been previously implanted. During initial implant, and prior to partial failure of lead 106" the low profile secondary header 160 was of course not present. In addition, the new IS-1 lead 180 was also not present. In the pre-existing configuration, there was an IS-1 pace sense lead 104 plugged into the atrial connector cavity 116b of the device header 114. The existing DF4 proximal lead connector 106a" was plugged directly into the DF4 connector cavity 118c of the device header 114. The pre-existing IS-1 lead 104 was routed from the device atrial connector cavity 116b intravenously into the right atrium 108. This IS-1 lead 104 has a distal tip electrode 104b and a distal ring electrode 104c. The four-conductor DF4 lead 106" was routed to a high-voltage shocking coil 128 in the superior vena cava 130 and to a second high-voltage shocking coil 132 located in the right ventricle 110. In addition, there were bipolar low-voltage conductors in lead 106" routed to a distal tip electrode 106b" and a distal ring electrode 106c", both of which were located in the right ventricular apex 110'. For this particular patient, at some point in time, there was a fracture or break 182 of the lead conductor 106" that connects to distal tip electrode 106b". In this example, a break or fracture is illustrated. However, there are many other conditions that can also result in the need for replacement of the low voltage pace sense functions of a DF4 lead. They would include insulation deterioration associated with low stimulation and or sensing resistance measurements at the time of patient presentation with symptoms or during routine clinic follow-up, poor pacing capture threshold, distal tip migration or micro perforation and the like. In this case, with a broken lead tip conductor 106b", the AIMD 100, 100B, which is a dual chamber ICD 100B with pacing functions, would no longer be able to pace the right ventricle. This condition can be life-threatening to a pacemaker dependent patient. In addition friction voltages generated by motion between the broken ends of the conductor can generate high frequency artifacts that the ICD must interpret as the life threatening abnormal heart rhythm ventricular fibrillation. Thus, at best, a patient may receive multiple painful shocks for no apparent reason. Further, many ICDs are currently implanted prophylactically and are never called upon to fire off their 100s of volt charges appropriately, but have still caused the death of their patient by unnecessary high voltage shocks thereby inducing the fatal arrhythmia the system was implanted to treat, but which the ICD 100B is then unable to correct.

Accordingly, rapid intervention by medical personnel is paramount. The low profile secondary header 160 of the present invention provides for a quick and simple solution. The patient's pectoral or other tissue pocket harboring the defective system is opened up so that the AIMD 100,100B is exposed. At this point, a new relatively small diameter lead 180 is inserted transvenously to a new location in the right ventricle 110, tested and repositioned as necessary until the best possible combination of pacing capture and sensing thresholds can be obtained. The new lead, 180 in FIG. 24, is shown in one such possible location, with its distal tip electrode 180b and associated ring electrode 180c just up from the RV apex 110', on the septum between the right and left ventricles. It should be noted that it is neither practical nor possible to just replace only the tip electrode circuit of a bipolar cardiac pacing lead. This is because the tip electrode and ring electrode act as a system. The separation between the tip and ring electrodes is very important in order to properly sense cardiac activity while also minimizing detection of stray noise, such as electromagnetic interference in the patient environment, and the sensing of electrical activity in other heart chambers, in skeletal muscle etc. Accordingly, the replacement lead 180 is a bipolar lead having two conductors and appropriately closely spaced tip 180b and ring 180c electrodes. It is plugged into replacement connector cavity 174 of the low profile secondary header 160. The pre-existing DF4 lead 106" is then plugged into the connector cavity 172 of the secondary header 160.

Figure 25:
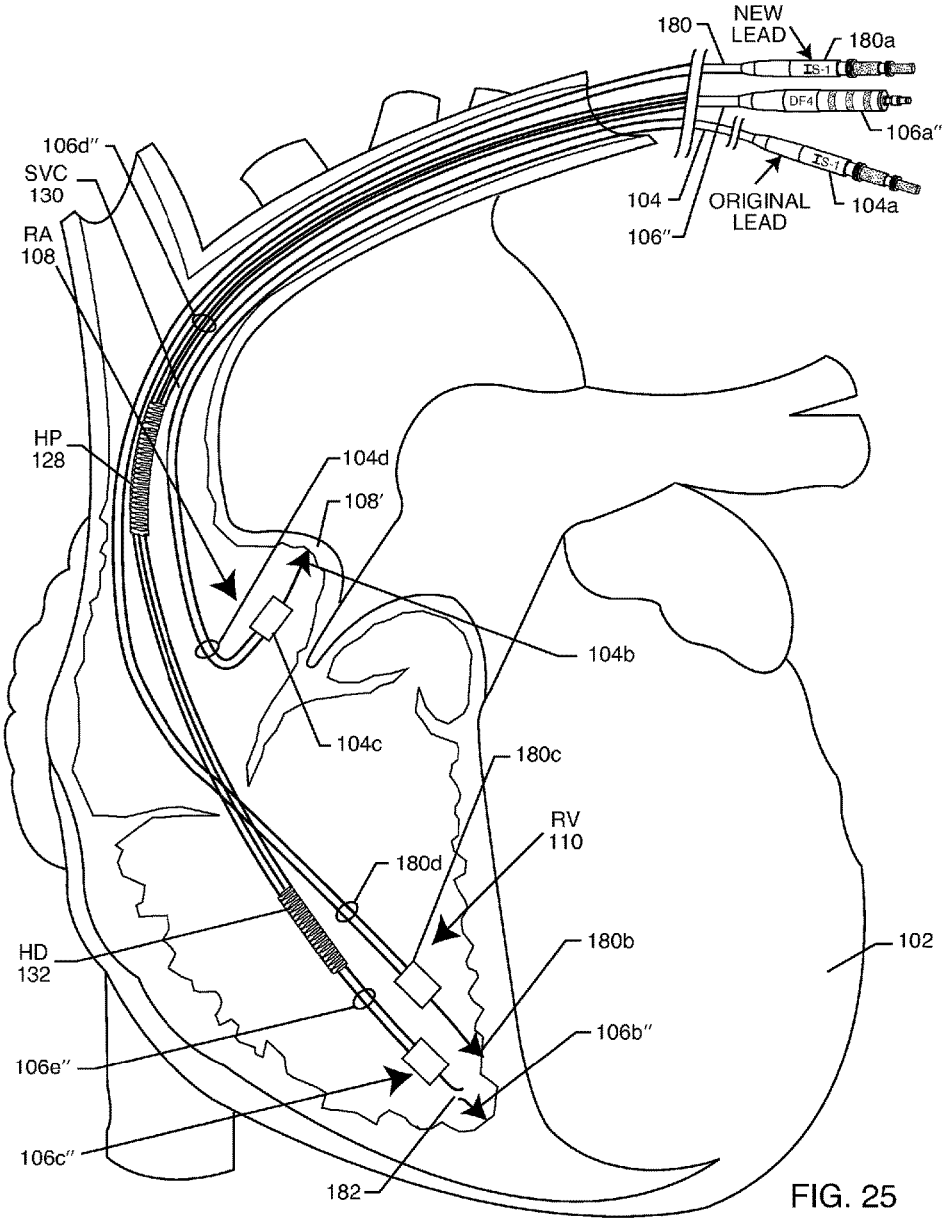
FIG. 25 illustrates the same lead system as previously illustrated in FIG. 24 except that all the lead conductors are shown.

FIG. 25 illustrates the human heart of FIG. 24 with all of the conductors in leads 106", 104 and 180 shown. The original and still functional lead 104 has two conductors 104d, one of which is routed to distal ring electrode 104c and the other conductor is routed to distal tip electrode 104b shown located in the right atrial appendage 108'. The original DF4 lead 106" has four conductors 106d". One of these conductors 106d" is routed to the high-voltage shocking coil 128 located in the superior vena cava 130. Another of these lead conductors 106d" is routed to a second high-voltage shocking coil 132 located in the right ventricle 110. The DF4 lead 106" also has bipolar low-voltage conductors 106e", one of which is routed to the distal ring electrode 106c" and another low-voltage conductor that was routed to distal tip electrode 106b". In this example, this conductor has fractured at location 182 such that the distal tip electrode 106b" is no longer in electrical contact with the AIMD 100, 100B electronic circuits. Also shown is the new lead 180 which is a bipolar IS-1 lead, which has two conductors 180d, one of which is routed to new distal ring electrode 180c and new distal tip electrode 180b. For simplicity, the low profile secondary header 160 and the device 100, 100B previously illustrated in FIG. 24 is not shown.

Figure 26A:
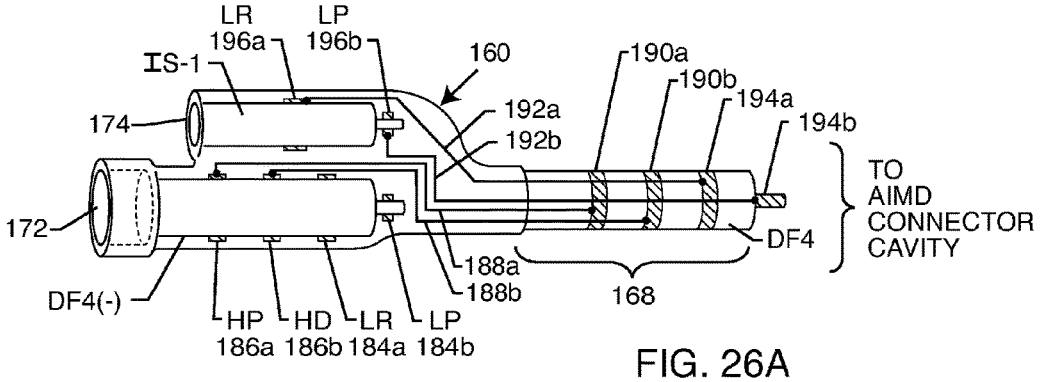
FIG. 26A is a pictorial-electrical view of the low profile conforming header of FIG. 24.

FIG. 26A shows the electrical connections for the low profile secondary header 160 from FIG. 24. It should be noted that in connector cavity 172, no electrical connections are made to the AIMD at contact points (LR) 184a and (LP) 184b. This disconnects the low-voltage functions LR and LP of the AIMD 100 from the DF4 secondary header connector cavity 172. It is very important to disconnect the LR and LP functions because the partially failed DF4 lead 106" to be reinserted into the low profile secondary header connector cavity 172 still has connections to distal ring electrode 160c", and also to the broken off portion 182 of the conductor that was previously routed to distal tip electrode 106b" in FIGS. 24 and 25, and can transmit a variety of inappropriate signals to confuse the pulse generator sensing circuits. It is very important that this noise not enter into AIMD circuitry where it could cause improper device function or false interpretation by AIMD software algorithms.

Accordingly, only the two high-voltage (HP) 186a and (HD) 186b contacts are connected in connector cavity 172 of the secondary header 160, which are connected to device 100B electronics after proximal connector plug 168 is reinserted into the appropriate device 100, 100c connector cavity. As previously noted, contacts 186a and 186b would still be reconnected to the two high-voltage shocking coils 128 and 132 as shown in FIG. 25. Referring once again to FIG. 26A, one can trace leadwires 188a and 188b routed from the contacts (HP) 186a and (HD) 186b to contact rings 190a and 190b of the secondary header plug 168 which is designed to be inserted into a DF4 connector cavity on the header 114 of the AIMD 100,100B. The contact rings 190a and 190b of proximal plug 168 conform to the ISO DF4 Standard for HP and HD high-voltage connections. One will also note that leadwires 192a and 192b are connected between the low-voltage connectors 194a, 194b on the secondary header DF4 proximal plug 168 and the contacts (LR) 196a and (LP) 196b in the replacement connector cavity 174 of the low profile secondary header 160.

It should also be noted that the shapes of the low profile secondary headers 160 shown in FIGS. 26A through 30C are straight or inline. The straight or inline shapes can certainly work, but are not the preferred embodiment. The preferred embodiment for the low profile secondary header 160 of the present invention was previously illustrated in FIGS. 11 through 24 wherein, the low profile secondary header 160 is low profile and conforms and fits very tightly to the adjoining surface of its AIMD 100, regardless of the shape of the latter.

Figure 26B:
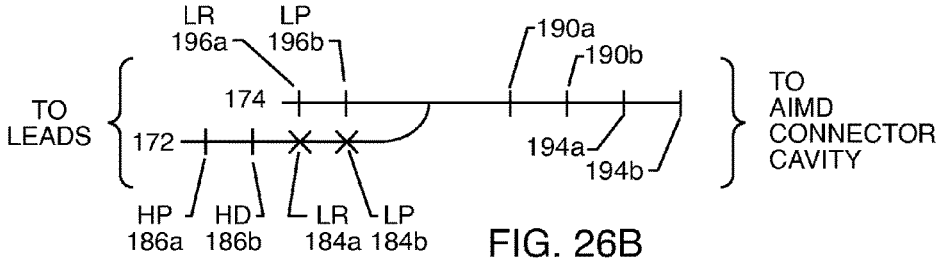
FIG. 26B is taken from FIG. 26A and illustrates a line drawing showing which electrical connections are active and which are inactive.
Figure 27A:
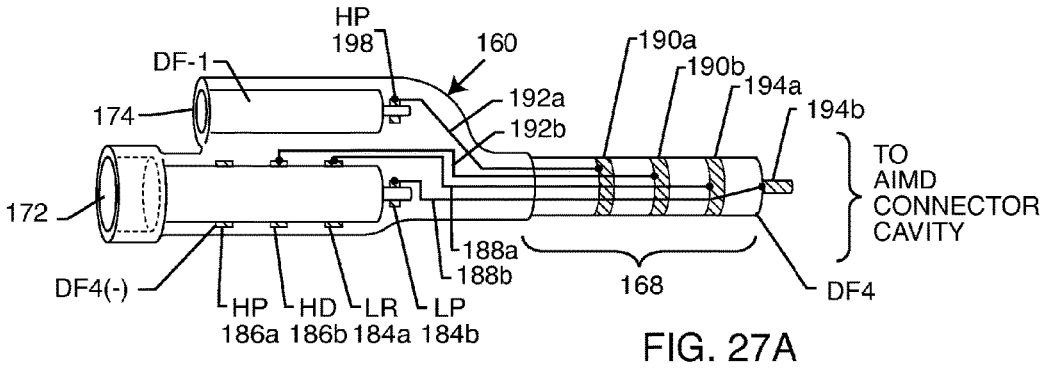
FIG. 27A is similar to FIG. 26A except that in this case illustrates that there has been a failure of the high-voltage shocking lead conductor leading into the superior vena cava coil electrode.

FIG. 26B is an electrical line diagram of FIG. 26A showing which electrical contacts are active and which are inactive. As can be seen, contacts (LR) 184a and LP 184b in connector cavity 172 have been disconnected so that the abandoned lead components cannot connect to AIMD electronic circuits. Secondary header 160 replacement connector cavity 174 has been provided for an IS-1 replacement lead. The low voltage contacts (LR) 196a and (LP) 196b have been provided in connector cavity 174 for a new IS-1 lead 180. It should be noted that in order to save some manufacturing time and material, it is possible in FIG. 26B that the electrical contacts 184a and 184b located in the secondary header 160 connector cavity 172 can be removed. This would save some material and manufacturing time, however, as it will be shown in subsequent drawings, it would be very useful to leave these contact points intact so that they may be connected to an energy dissipating surface (EDS) to pull RF energy out of the abandoned lead conductors during MRI procedures FIG. 27A is very similar to FIG. 26A except that in this case, there has been a failure of the lead conductor in lead 106" from FIG. 24, that is routed to the high-voltage shocking coil (HP) 128 that's located in the superior vena cava 130. In this case, contact 186a has been disconnected in the secondary header 160 connector cavity 172 so that no interference or short circuiting can affect the AIMD electronics. The selective deletion of electrical contacts has led us to denote the secondary header connector cavity 172 as DF4(−). However, DF4(−) should be considered generic for any secondary header DF4 like configuration with one or more electrode contact site disconnections. In accordance with the present invention, a secondary header 160 DF-1 lead replacement connector cavity 174 has been provided so that a new high-voltage shocking coil lead in accordance with the DF-1 Standard can be inserted transvenously and then plugged into the secondary header 160 replacement connector cavity 174. Contact (HP) 198 in the replacement connector cavity 174 replaces contact (HP) 186a in connector cavity 172 and is routed to contact ring 190a by leadwire 192a.

Figure 27B:
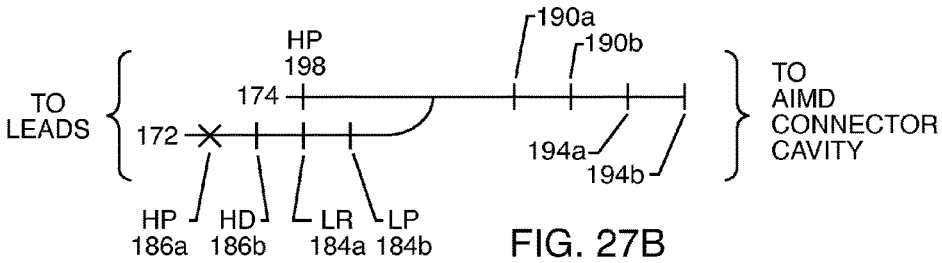
FIG. 27B is a line diagram taken from FIG. 27A illustrating which electrical connections are active and which are inactive.

FIG. 27B is an electrical line diagram derived from FIG. 27A showing which electrical contacts are active and which are inactive. As can be seen, high-voltage contact 186a in the 172 connector cavity has been disconnected from the secondary header 160 connector ring 190a.

Figure 28A:
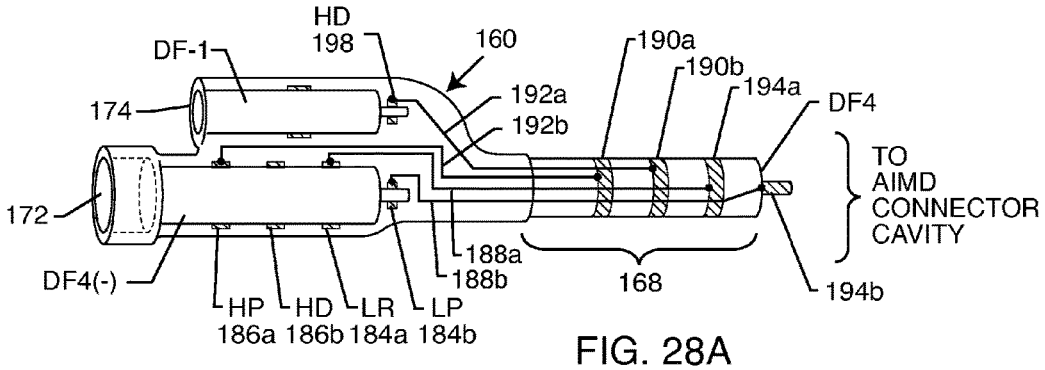
FIG. 28A is similar to FIG. 26A except that in this case, there is a failure in the conductor or some other lead component associated with the high-voltage shocking coil located in the right ventricle.

FIG. 28A is very similar to FIGS. 26A and 27A. In this case however, there has been a failure of the conductor that is routed to the distal high-voltage shocking coil (HD) 132 as shown in the right ventricle 110 in FIG. 24. The secondary header DF-1 replacement connector cavity 174 is provided so that a new high-voltage shocking coil DF-1 lead can be routed transvenously down into the right ventricle. This contact 186b has been disconnected in the connector cavity 172.

Figure 28B:
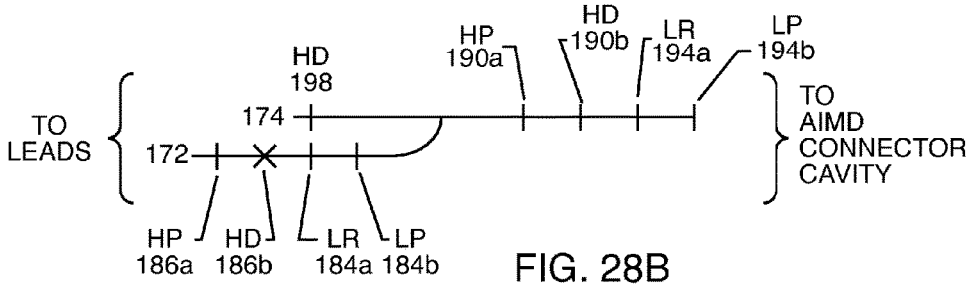
FIG. 28B is a line diagram taken from FIG. 28A illustrating which electrical connections are active and which are inactive.

FIG. 28B is an electrical line diagram taken from FIG. 28A showing which electrical contacts are active and which are inactive. As can be seen, in the low profile secondary header 160 connector cavity 172, the high-voltage contact (HD) 186b has been disconnected from contact ring 190b of the secondary header 160 connector plug 168. It is this lack of electrical wiring that will disconnect the abandoned components of the partially failed DF4 lead from any contact with AIMD electronics, after the new DF-1 lead and the reused, partially failed, DF4 lead are plugged into a secondary header 160 that is inserted into the DF4 connector cavity on the header of the original ICD. Contact (HD) 198 in the replacement connector cavity 174 replaces contact (HD) 186b in connector cavity 172 and is routed to contact ring 190b by leadwire 192a.

Figure 29A:
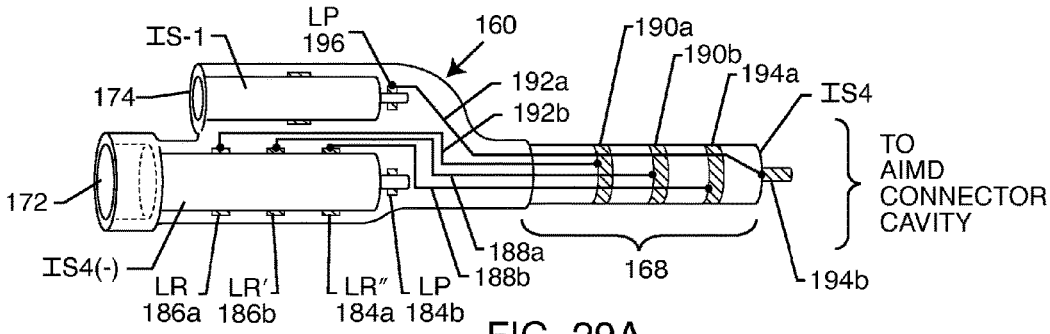
FIG. 29A illustrates a low-voltage IS4 low profile conforming secondary header wherein, the distal tip electrode conductor has failed.
Figure 29B:
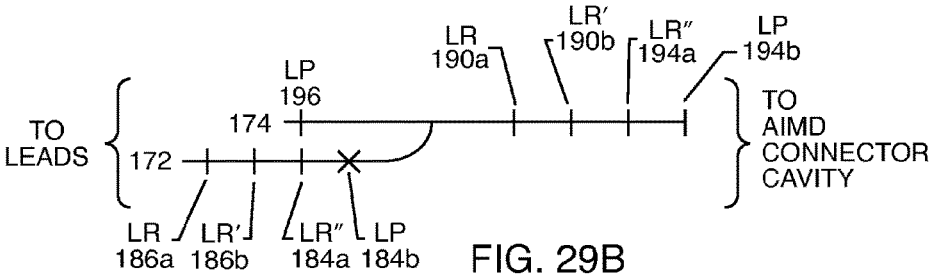
FIG. 29B is a line diagram taken from FIG. 29A illustrating which electrical connections are active and which are inactive.

FIG. 29A presents a completely different situation. This illustrates a low profile secondary header 160 with an IS4 low-voltage quadripolar connector and two connector cavities, one IS-1 cavity 174 and one IS4(−) cavity 172. One is referred to lead 104''' in FIG. 5 to see how an IS4 lead 104''' is routed through the coronary sinus 138 and into an epicardial vein 140, 142 near the lateral surface of the left ventricle 136. In this particular example, in FIG. 29A, there has been a lead 104''' conductor failure such that the tip electrode 144d of FIG. 5, is no longer functional. Accordingly, as shown in FIG. 29A, there is no wire connection to tip LP 184b in the secondary header 160 IS4(−) connector cavity 172. This disconnection is important so that stray noise and short circuiting cannot affect AIMD circuitry, after all connections to the secondary header 160 and of the secondary header to the usually original AIMD 100, 100B, and reimplantation of the reconfigured system have been completed. As can be seen, leadwire 192a has been disconnected from point (LP) 184b in the IS4(−) connector cavity 172. Instead leadwire 192a has been rerouted to connection tip point (LP) 196 in IS-1 replacement connector cavity 174. This allows a new lead to be transvenously or transthoracically inserted into, or attached to, the left ventricle, and then plugged into this replacement connector cavity 174. As after the partial failure of a IS4 low voltage lead, the still functional components of the IS4 lead are reconnected by insertion of its IS4 connector into the IS4 (−) secondary header connector cavity 172. FIG. 29A demonstrates repair of an IS4 lead partial failure by using a new unipolar IS-1 lead plugged into replacement connector cavity 174. Any pair of the ring electrodes on plug 168 in FIG. 29A could also be disconnected from their respective electrodes in connection cavity 172, and repair accomplished using a bipolar IS-1 lead. FIG. 29B is a line diagram showing which connections are active and inactive in connector cavities 172 and 174 from FIG. 29A.

Figure 30A:
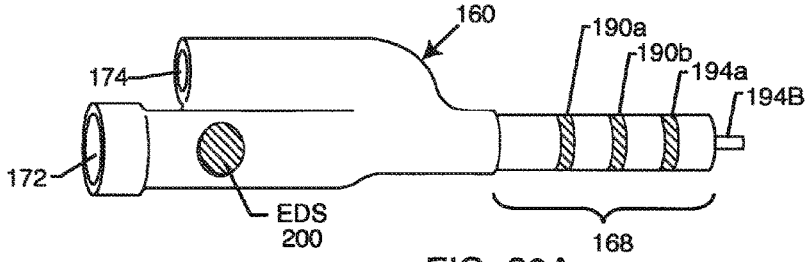
FIG. 30A illustrates a pictorial view of the low profile secondary header of the present invention showing an energy-dissipating surface (EDS) for dissipating MRI induced RF energy.

FIG. 30A is an overall isometric view of a secondary header 160 of the present invention. As previously noted, it is laid out in a straight line to facilitate the ease of drawing electrical diagrams. Although a straight line form factor for the low profile secondary header 160 is certainly one option, the preferred embodiment is a low profile shape that tightly conforms to the associated AIMD's housing 112 and/or header block 114. One is referred to FIGS. 11 through 23 for examples as to the preferred low profile secondary header 160 AIMD 100 low profile conforming shapes. What is unique about the structure shown in FIG. 30A is the addition of energy dissipating surface (EDS) 200. Generally, this is a metallic surface, such as stainless steel or titanium or the like, which is in direct contact with the body tissues and fluids in the area of the pectoral pocket (or other location).

Figure 30B:
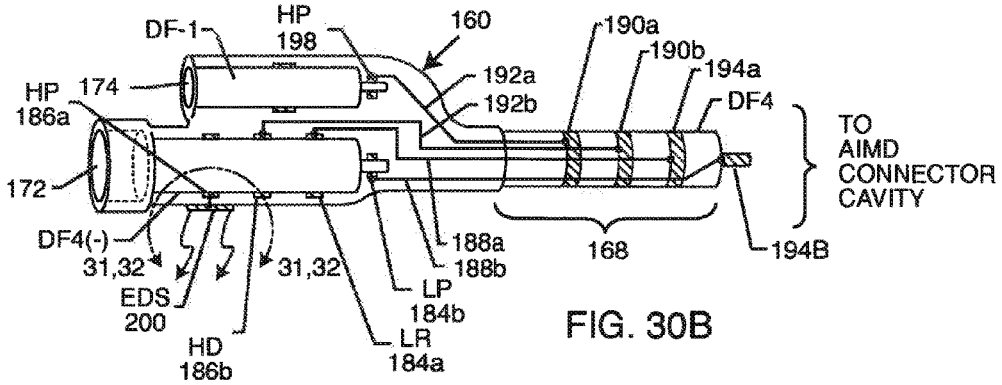
FIG. 30B is a pictorial section illustrating the electrical connections from FIG. 30A.

FIG. 30B is very similar to FIG. 27A showing the same DF4(−) configuration in a low profile secondary header 160. Like in FIG. 27A, 30B presents a low profile secondary header 160 designed to correct a situation where there has been a failure of the lead conductor that is routed to the shocking coil (HP) 128 located in the superior vena cava 130. As in FIG. 27A, there is no leadwire connecting the electrical ring (HP) 186a from the connector cavity 172 to connector plug contact ring 190a. However, there is a major difference from FIG. 27A illustrated in FIG. 30B, as this abandoned conductor connection HP 186a is now electrically connected to the energy dissipating surface (EDS) 200 of FIG. 30A. This is very important considering the marked increase in the need for MRI diagnostic interventions in general, and particularly in the type of heart patient requiring AIMDs, as it has been shown that conductors in abandoned leads can pick up substantial RF energy from the MRI RF-pulsed field. One is referred to U.S. Patent Publication 2010/0324639 for a more thorough description of the problems associated with abandoned leads and how energy dissipating surfaces can alleviate overheating of such leads. One is also referred to U.S. Patent Publication 2010/0217262, which also describes energy dissipating surfaces. Both of these patent publications are incorporated herein by reference.

Figure 30C:
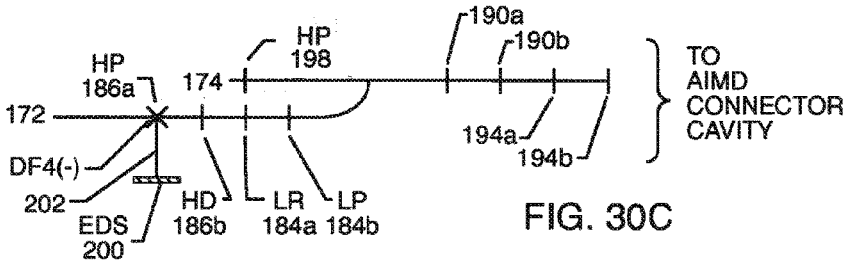
FIG. 30C is a line diagram taken from FIG. 30B showing which electrical connections are active and which are inactive. It also shows that the malfunctioning HP components of the DF4 lead have been disconnected from the secondary header connector but routed to an energy dissipating surface.

FIG. 30C is an electrical line diagram of FIG. 30B showing which electrical contacts are active and inactive in connector cavities 172 and 174. As one can see, the inactive contact 186a in connector cavity 172 is shown electrically connected directly to the energy dissipating surface (EDS) 200, by leadwire 202.

Figure 31:
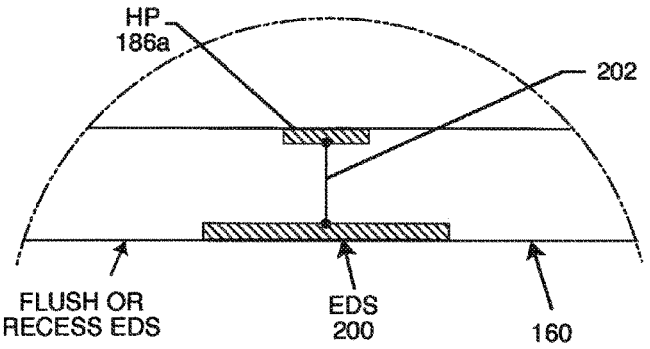
FIG. 31 is a cross-sectional view taken generally from section 31-31 from FIG. 30B and illustrates that the energy dissipating surface may be recessed or mounted flush with the low profile secondary header surface.

FIG. 31 is a partial section view taken from section 31-31 from FIG. 30B. It shows that the energy dissipating surface 200 can be flush or even recessed into the generally smooth body of the low profile secondary header 160. To see how dangerous abandoned leads can be in an MRI environment, one is again referred to the article entitled, PACEMAKER LEAD TIP HEATING AND ABANDONED AND PACEMAKER-ATTACHED LEADS AT 1.5 TESLA MRI. Reference journal of Magnetic Resonance Imaging 33:426-431 (2011). FIG. 2 of this paper shows that abandoned pacemaker leads that are capped (not connected to an AIMD) can heat as much as 31° C. at the distal electrode over body temperature. This is an extremely dangerous condition that would cause damage to adjacent cardiac tissue. The low profile secondary headers 160 of the present invention, when they do not have an energy dissipating surface EDS, act very similar to an abandoned capped lead. In other words, when the proximal partially failed leads DF4 or IS4 connector is inserted into connector cavity 172 of the low profile secondary header 160, the lead contacts are then electrically insulated from coming into contact with body fluids or tissues. Accordingly, it is very important to provide an energy dissipating surface feature so that the RF energy that's picked up in the abandoned lead conductor can be harmlessly dissipated as energy diverted into the tissue surrounding the AIMD 100 pocket. It is also interesting to note why abandoned leads are more dangerous than a connected lead. This is because leads properly connected into a pulse generator header benefit from the prior art EMI filter feedthrough capacitors that are present at the point of primary header, connector wire ingress 124 into modern AIMDs. This filter capacitor presents a very low impedance at MRI RF frequencies thereby substantially connecting the lead conductor to the metallic housing 112 of the AIMD as in FIGS. 2 through 5. In this case, the AIMD housing 112 acts as a very effective energy dissipating surface. The location and operation of these prior art feedthrough capacitors is more thoroughly described in U.S. Pat. Nos. 4,424,551; 5,333,095; 5,905,627; and 6,765,780. MLCC capacitors can also be very effective energy diverters as described in U.S. Pat. Nos. 5,896,267 and 5,650,759. All of the aforementioned patents are incorporated herein by reference.

Figure 32:
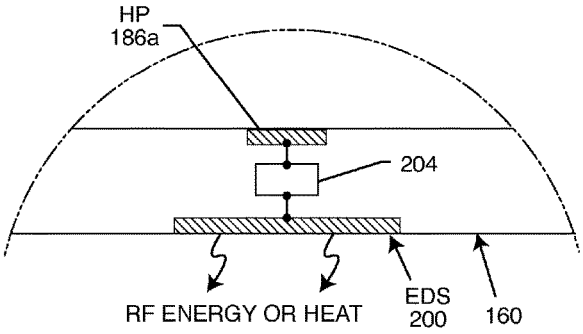
FIG. 32 is very similar to FIG. 31 except that it illustrates that the connection between the abandoned lead and the energy dissipating surface may be a frequency selective diverter element.

FIG. 32 is similar to FIG. 31 except that the leadwire 202 has been replaced by a general frequency selecting diverter element 204.

Figure 33:
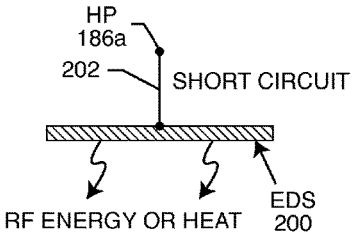
FIG. 33 illustrates that the diverter of FIG. 32 can be a short circuit or a direct connection.

FIG. 33 illustrates that the diverter element 204 can simply be a leadwire or short circuit 202 to the energy dissipating surface 200 as previously illustrated in FIG. 31.

Figure 34:
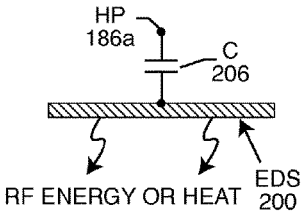
FIG. 34 illustrates that the frequency selected diverter or FIG. 32 can be a capacitor.

FIG. 34 shows that the diverter element 204 of FIG. 32 can be a capacitor (C) 206. The frequency selective diverter element capacitor 206 has a capacitive reactance. As more thoroughly described in U.S. Patent Publication 2010/0324639, the reactance, such as a capacitive reactance, can help to cancel a lead conductor source impedance which could be primarily inductive. In this way, maximal energy transfer can be accomplished from the abandoned implanted lead conductor to the energy dissipating surface 200. In other words, a short circuit 202, as illustrated in FIGS. 31 and 33, may not draw the maximal energy out of the lead.

Figure 35:
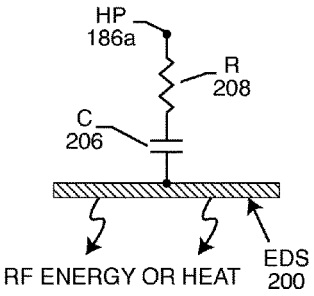
FIG. 35 illustrates that the diverter of FIG. 32 can be a resistor in series with a capacitor.

FIG. 35 illustrates a resistor (R) 208 in series with the capacitor 206 as previously illustrated in FIG. 34. In this case, the resistance would match the characteristic resistance of the implanted (abandoned) lead conductor.

Figure 36:
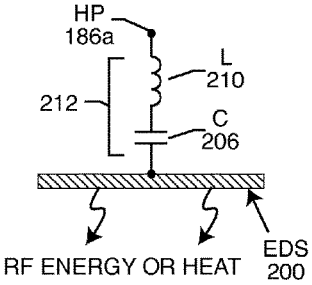
FIG. 36 illustrates that the diverter of FIG. 32 can be an inductor in series with a capacitor forming an L-C trap filter.

FIG. 36 illustrates that the diverter element 204 shown in FIG. 32 may consist of an inductor (L) 210 in series with a capacitor 206, which is also known as an L-C trap filter 212. In general, this L-C trap 212 would be tuned to be resonant at the MRI RF pulsed center frequency.

Figure 37:
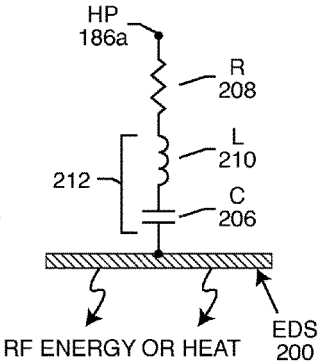
FIG. 37 illustrates the trap filter of FIG. 36 with a resistor added in series.

FIG. 37 is very similar to FIG. 36 and shows a resistive element 208 in series with the inductor 210 and capacitor 206 of the L-C trap filter 212. This resistor element 208 is important to control the Q or 3-dB bandwidth of the resonant trap filter 212 and also can be tuned for maximal energy transfer to the energy dissipating surface 200. Again, one is referred to U.S. 2010/0324639, the contents of which are incorporated herein by reference.

Figure 38A:
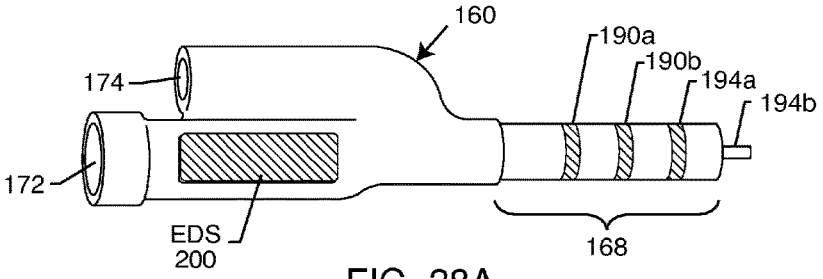
FIG. 38A illustrates that the energy dissipating surface can be larger.

FIG. 38A is very similar to FIG. 30A except that the energy dissipating surface 200 has been enlarged. A larger energy dissipating surface 200 means that more energy can be dissipated into surrounding body fluids and tissues without a significant increase in temperature on the energy dissipating surface 200.

Figure 38B:
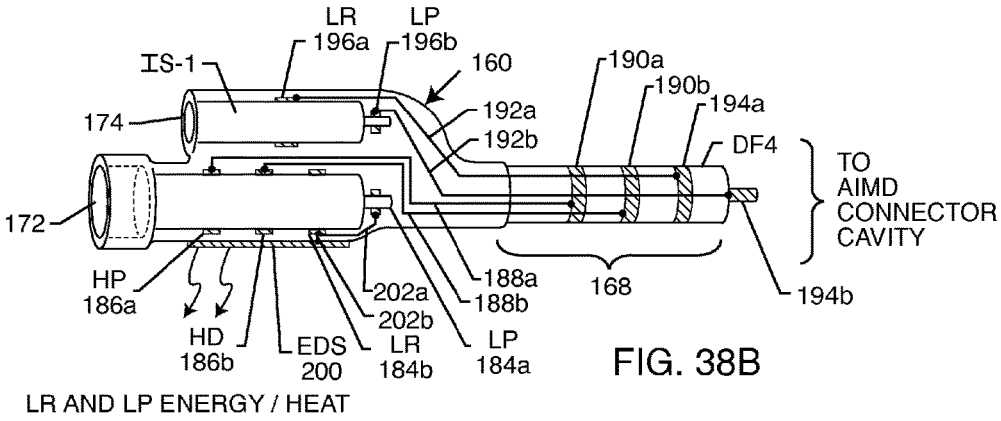
FIG. 38B illustrates an electrical schematic diagram of the low profile secondary header from FIG. 38A.

FIG. 38B is a pictorial electrical schematic diagram taken from FIG. 38A. In this case, the low profile secondary header 160 has been designed to deal with a failure of the bipolar low-voltage components of a DF4 lead so that contacts (LR) 184b and (LP) 184c in connector cavity 172 are not connected to contact ring 194a and contact tip 194b in the secondary header 160 connector plug 168. As described, in FIG. 24, this can represent a failure of a low voltage conductor that's either routed to the distal tip electrode 106b or the ring electrode 106c or both. Looking carefully at FIG. 38B, one can see that leadwires 192a and 192b have been routed to contacts (LR) 196a and (LP) 196b in the replacement connector cavity 174, which are in turn connected to low-voltage contact ring 194a and contact tip 194b in connector plug 168. Importantly, the two abandoned low-voltage connections (LP) 184a and (LR) 184b in connector cavity 172 have been disconnected from possible contact with AIMD electronic circuits after leads have been plugged into connector cavities 172 and 174 and plug 168 is plugged into the ICD, while at the same time, both abandoned lead connection (LP) 184a and (LR) 184b are connected to the enlarged energy dissipating surface 200 via connecting wires 202a and 202b. Accordingly, not only are the two low-voltage lead conductors (LR) 184a and (LP) 184b disconnected from AIMD electronics, they are also connected so as to divert dangerous RF energy to the energy dissipating surface 200 in an MRI environment. Any of the energy diverting circuits of FIGS. 33 through 37 may, of course, be used. This greatly increases patient safety (for example, if an emergency MRI scan is needed).

Figure 38C:
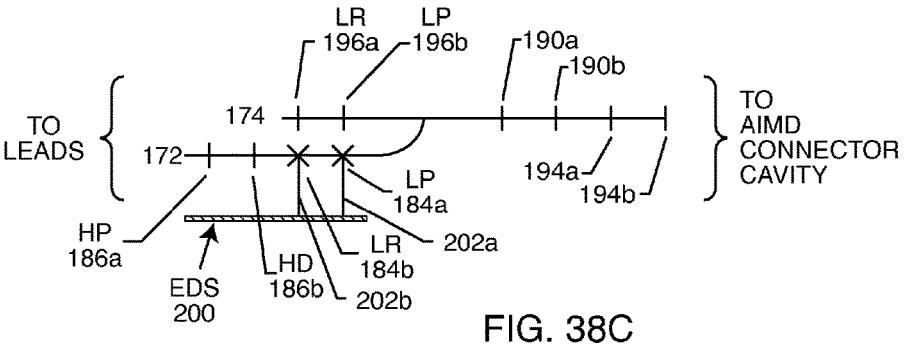
FIG. 38C illustrates a line diagram taken from FIG. 38B showing which electrical connections are active and which are inactive.

FIG. 38C is an electrical line diagram taken from FIG. 38B showing which electrical connections are active and which are inactive. As can be seen, electrical connections (LR) 184b and (LP) 184a in connector cavity 172 have been disconnected from the proximal connector plug 168, but are also connected through leadwires 202a and 202b to the energy dissipating surface 200.

Figure 39A:
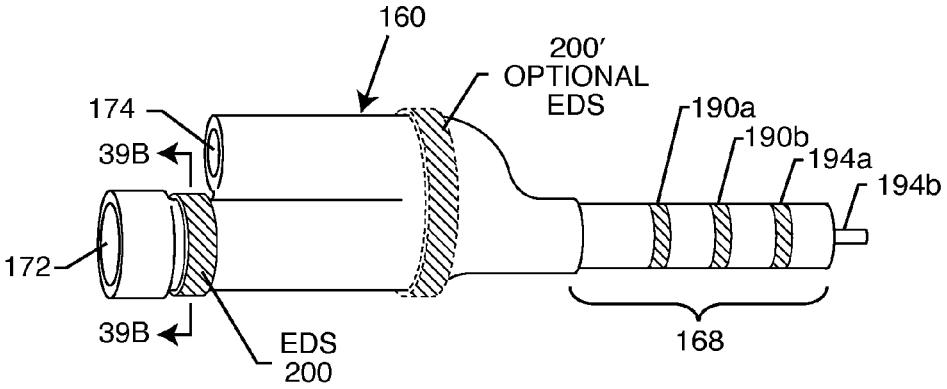
FIG. 39A is similar to FIGS. 30A and 38A illustrating that the energy dissipating surface can be a circularly shaped ring.

FIG. 39A is very similar to FIGS. 30A and 38A except that, in this case, the energy dissipating surface 200 is a ring located around the connector cavity 172. There could be a second or even optional ring 200' located around the entire housing of the low profile secondary header 160 as shown. These EDS rings 200, 200' can be of varying widths as required to dissipate sufficient RF energy during MRI scans. The rings 200, 200' can be round or oval as shown. Any shape can be used as long as it conforms tightly to the shape of the secondary header 160. In a preferred embodiment, they would be flush with the surfaces of low profile secondary header 160.

Figure 39B:
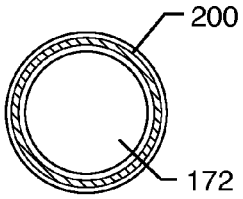
FIG. 39B is a cross-sectional view taken from section 39B-39B of FIG. 39A.

FIG. 39B is a sectional view taken generally from section 39B-39B from FIG. 39A. Referring to FIG. 39B, one can see the sectional view of the conductive energy dissipating surface ring 200 which, in this case, is round.

Figure 40:
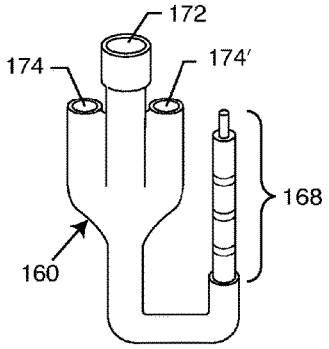
FIG. 40 illustrates that the secondary header has three ISO connector cavities.

FIG. 40 is a low profile secondary header 160 of the present invention, except in this case; there are three connector cavities 172, 174 and 174'.

Figure 40A:
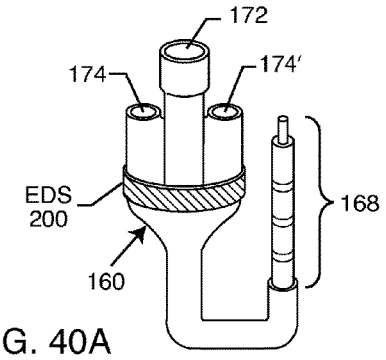
FIG. 40A illustrates a tripolar secondary header of the present invention that has a ring shaped energy dissipating surface.

FIG. 40A is a tripolar secondary header of the present invention that is similar to FIG. 40, but an oval or elliptical energy dissipating surface 200 has been added. It has two replacement connector cavities 174 and 174'. Cavity 174 is for an abandoned lead, such as an IS-1, a DF-1 so that the abandoned lead conductors and their associated electrodes are safer during MRI scans. In some models cavity 174 could even be DF4 or IS4 or the like, so as to improve MRI compatibility of additional abandoned quadripolar leads. This may seem an unlikely situation to an engineer or other technical person, but physicians specializing in lead extraction not infrequently are presented with infected patients in whom 3 or more leads have been abandoned, in addition to whatever leads continue to be functional. As previously described, connector cavity 172 is to receive a DF4 or IS4 proximal lead connector wherein, one of the lead conductors or other components has failed. Secondary connection cavity 174 and/or 174' is for implantation of a new lead to replace the failed function(s) of the previously implanted IS4 or DF4 lead.

Figure 40B:
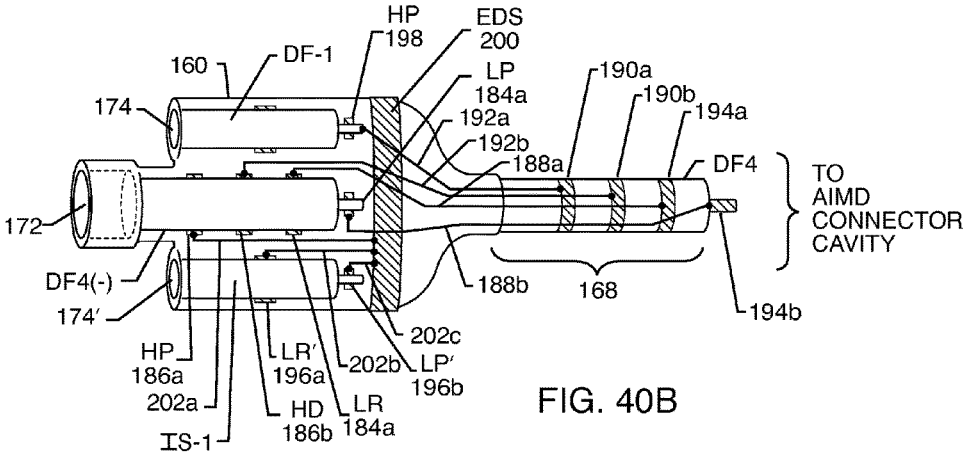
FIG. 40B is a pictorial-electrical diagram taken from FIG. 40A illustrating the secondary header wiring connections for replacing a failed or dysfunctional DF4 proximal coil circuit, and for connecting it's failed conductors as well as the conductors of a separately failed IS-1 lead to an energy dissipating surface.

FIG. 40B is a pictorial-electrical diagram derived from FIG. 40A illustrating some possible wiring connections. Referring to connector cavity 172, one can see that the high-voltage proximal contact (HP) 186a has been disconnected from plug 168 and instead routed to the energy dissipating surface 200 by wire 202a. This has the desired effect of connecting the defective conductor of a subsequently inserted lead to the energy-dissipating surface 200 so that it will be safer during MRI scans. A secondary DF-1 connector cavity 174 has been provided for receipt of the proximal connector of a newly implanted high-voltage DF-1 lead, after it has been routed into the superior vena cava (not shown). In this case, leadwire 192a connects the electrode (HP) 198 in the 174 connector cavity to connector plug 168 ring contact electrode 190a. As before, the secondary header 160 proximal connector plug 168 is designed to be inserted into the appropriate AIMD connector cavity. In this case, provision is also made for connecting both conductors of a defective IS-1 lead to the energy dissipating surface (EDS) 200 by means of leadwires 202b and 202c. For example, the atrial lead as previously described in FIGS. 4 and 24 could also have failed and been replaced and 174' provides a place to plug in this abandoned lead and provide an additional MRI safety feature. By extension, instead of the original atrial lead in FIG. 24, the replacement IS-1 ventricular lead could have failed, and could be similarly replaced and made MRI compatible. Further if there had been partial failure of the DF4 lead plus failure requiring replacement of both IS-1 leads in FIG. 24 a four connector port secondary header 160 is readily understood as another configuration. Note that the secondary header 160 connector cavity 174' shown in FIG. 40 provides for both the tip and ring connections (LP') 196a and (LR') 196b to be connected to the energy dissipating surface 200 by way of leadwires 202b and 202c. In this way, all of the abandoned lead conductors are attached to an energy dissipating surface 200 for dissipation of RF energy when the patient is exposed to high-power MRI scans. One is also referred to U.S. Pat. No. 8,000,801 entitled, SYSTEM FOR TERMINATING ABANDONED IMPLANTED LEADS TO MINIMIZE HEATING AND HIGH-POWER ELECTROMAGNETIC FIELD ENVIRONMENTS, the contents of which are incorporated herein by reference. One is also referred to U.S. Patent Publication 2010/0324639 entitled, METHODOLOGY AND APPARATUS TO TERMINATE ABANDONED ACTIVE IMPLANTABLE MEDICAL DEVICE LEADS; and U.S. Patent Publication 2011/0022140 entitled, METHODOLOGY AND APPARATUS TO TERMINATE ABANDONED ACTIVE IMPLANTABLE MEDICAL DEVICE LEADS; and U.S. Patent Publication 2010/0217262 entitled, FREQUENCY SELECTIVE PASSIVE COMPONENT NETWORKS FOR ACTIVE IMPLANTABLE MEDICAL DEVICES UTILIZING AN ENERGY DISSIPATING SURFACE. The contents of all of the aforementioned patent publications are incorporated herein by reference.

Figure 40C:
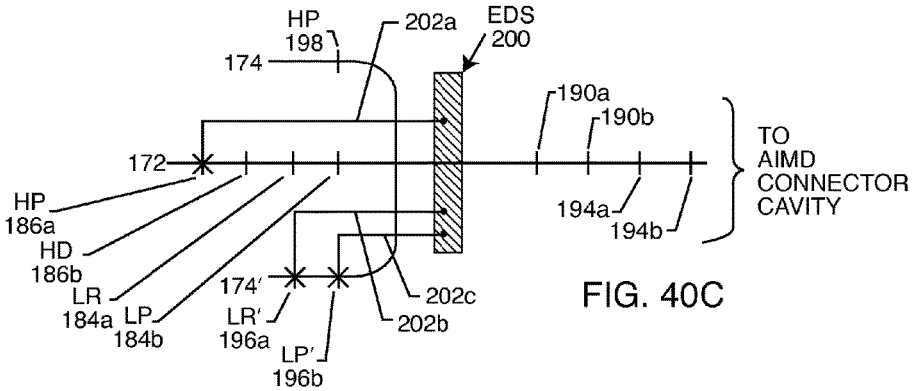
FIG. 40C is an electrical line diagram taken from FIG. 40b showing which electrical connections are active and which are inactive.

FIG. 40C is an electrical line diagram taken from FIG. 40B showing which electrical connections are active and which are inactive. As one can see, in the DF4(−) low profile secondary header 160 extension cavity 172, connection (HP) 186a is inactive, meaning that it is no longer connected to the secondary header connector plug 168 and contact 190a will no longer be connected to the defective lead. Connections (HD) 186b, (LR) 184a and (LP) 184b are in contrast all active, meaning that in the future following appropriate connections and implantation, those will continue to be connected to AIMD circuitry. Importantly, the inactive electrode (HP) 186a, which would have been routed to the proximal high-voltage shocking coil, has instead been connected to the energy dissipating surface 200 by way of leadwire 202a. A connector cavity 174 in the low profile secondary header 160 for a new lead has been provided. This is a DF-1 connection, meaning that a new DF-1 lead can be plugged in and routed down toward the superior vena cava 130 to replace the defective defibrillation coil originally connected to the equivalent electrode (HP) 186a on the partially failed DF4 lead. In addition, there is another connector cavity 174' provided for a low voltage abandoned IS-1 lead, for example lead 104 as previously described in FIG. 24.

In summary, the structure for low profile secondary header 160 as illustrated in FIGS. 40A through 40C combines the present invention with an abandoned lead cap as previously described in U.S. Patent Publication 2010/0324639.

Figure 41:
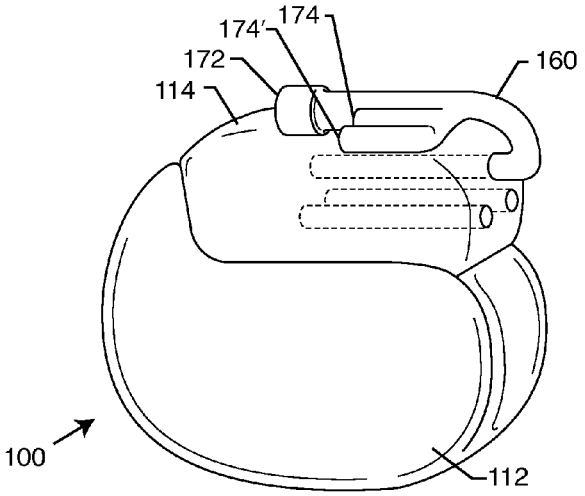
FIG. 41 shows the secondary header of FIG. 40 inserted into a connector cavity of an AIMD.

FIG. 41 illustrates the three-connector cavity low profile secondary header 160 of FIG. 40 wherein, the secondary header 160 has been plugged into a DF4 or IS4 connector cavity of the device 100 header 114 connector cavity.

Figure 42A:
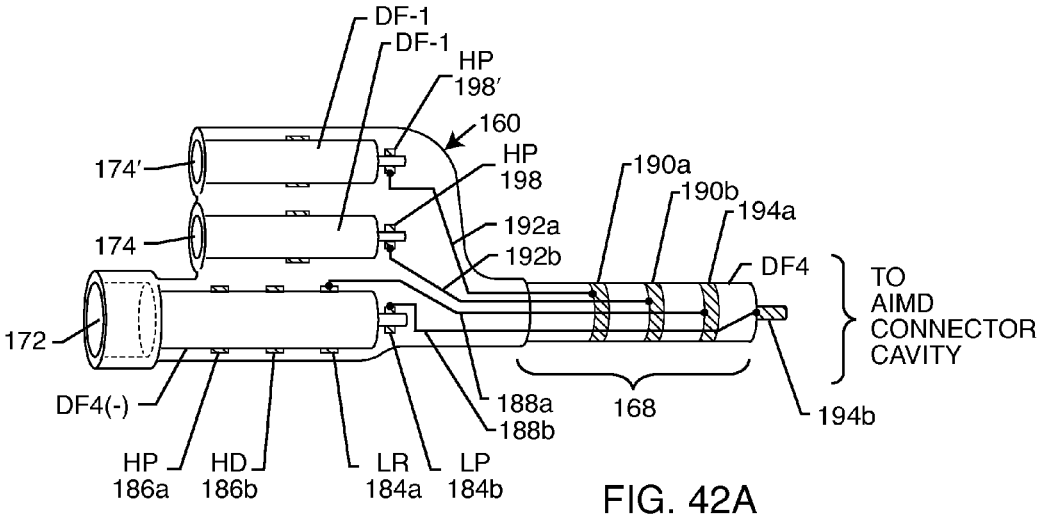
FIG. 42A is the electrical schematic diagram of the secondary header shown in FIG. 40 wherein both high voltage circuits of the original DF4 lead have failed and their electrodes have been disconnected from AIMD electronics in the secondary headers DF4 connector cavity. The secondary header therefore also provides DF-1 connector cavities for two supplementary DF-1 leads.

FIG. 42A is one type of electrical diagram for another embodiment of a triple connector cavity 172, 174 and 174' secondary header 160 of FIG. 41. This type of arrangement would be used, for example, in the case where both of the high-voltage shocking coil conductors of lead 106", as previously illustrated in FIG. 25, have failed. One can see that both DF4(−) electrodes (HP) 186a and (HD) 186b in connector cavity 172 have been disconnected from contacts in plug 168. Accordingly, there are two secondary header DF-1 connector cavities 174 and 174' illustrated. In this case, two new shocking leads would be required. One placed in the superior vena cava 130 and the other placed into the right ventricle 110 in parallel with the existing leads.

Figure 42B:
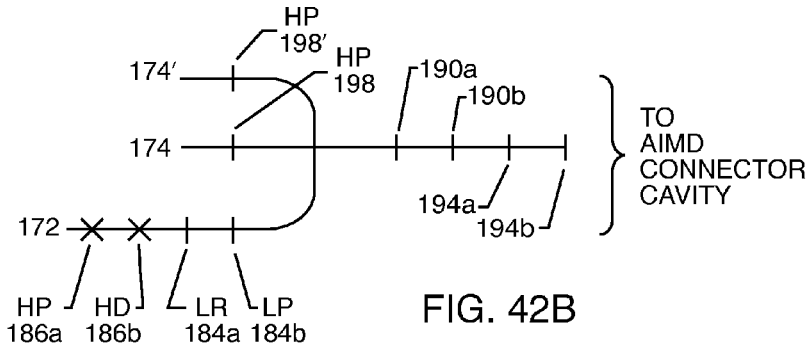
FIG. 42B is a line diagram taken from FIG. 42A illustrating which electrical contacts are active and which are inactive.

FIG. 42B is an electrical line drawing derived from FIG. 42A showing which secondary header connector cavity electrical contacts are active and which are inactive. Of course, in the preferred embodiment, the inactive locations would be connected to an energy dissipating surface 200 as previously described in FIG. 30A, 38A or 39A. It should also be noted, that in designs where it was decided not to incorporate an energy dissipating surface, then it would not be necessary to provide connector electrode rings for abandoned circuits inside the connector cavity 172. For example, referring to FIG. 42A, the abandoned ring contacts (HP) 186a and (HD) 186b could simply be eliminated from the low profile secondary header 160 which would save some cost in manufacturing and materials.

Figure 43:
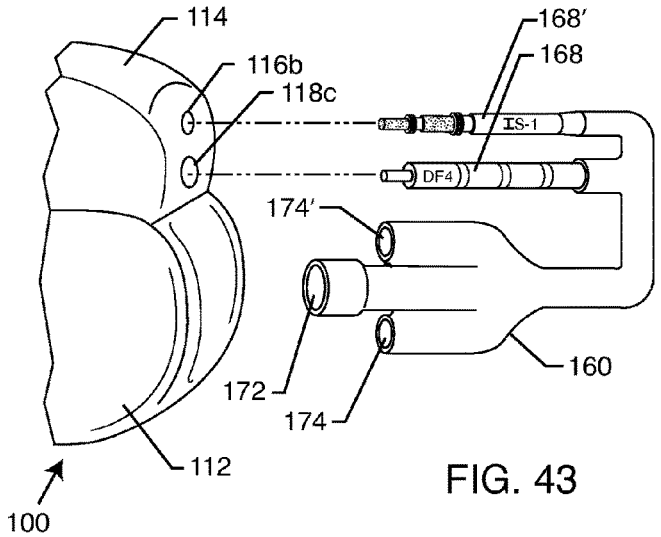
FIG. 43 illustrates the secondary header having two secondary male connectors, one of which is a convenient passthrough.

FIG. 43 is very similar to FIG. 40 except that there are two low profile secondary header 160, connector plugs IS-1 168' and DF4 168 that are designed to be inserted into connector cavities 116b and 118c of AIMD 100 header 114. In this case, the secondary header 160 IS-1 plug 168' provides for an electrical pass-through. This is better understood by referring to FIG. 44A.

Figure 44A:
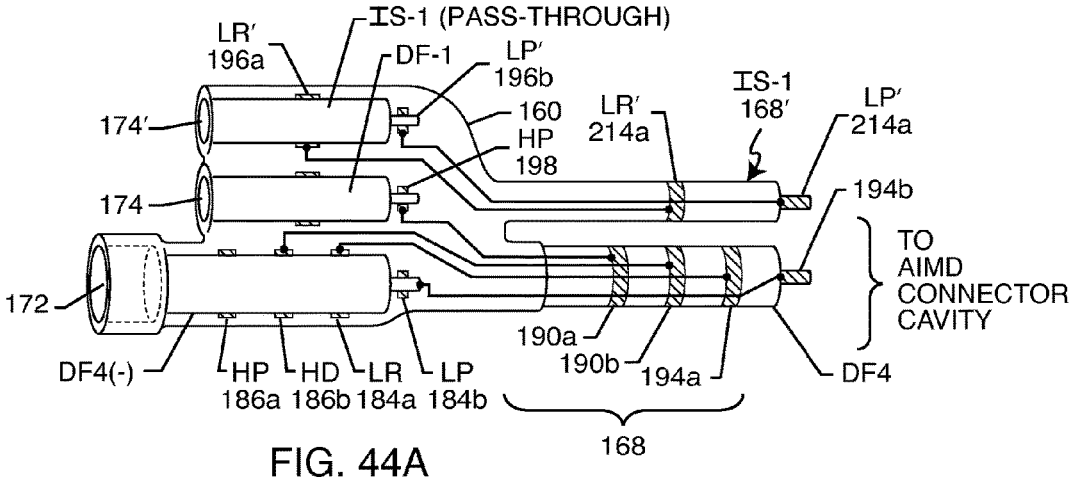
FIG. 44A illustrates an electrical schematic diagram taken from the secondary header of FIG. 43.

FIG. 44A is a pictorial electrical wiring diagram taken from FIG. 43. The physical shape in FIG. 44A has been changed to illustrate that secondary header connector cavities 174 and 174' can be aligned side by side next to connector cavity 172 or on both sides of connector cavity 172, as previously illustrated in FIG. 43. A low profile conforming shape that tightly hugs the device 100 and/or its header 114 is preferred. Referring once again to FIG. 44A, one can see that the IS-1 secondary header connector plug 168' passes its electrical connections straight through to secondary header connector cavity 174'. The purpose of this type of pass-through is so that the new and old leads can all be lined up together, which facilitates winding and dressing the leads together so that they do not splay or cross over and can make for a more compact configuration in a device pocket. In other words, the pass-through feature consisting of connector IS-1 plug 168' and connector cavity 174' is provided as an additional convenience, in order to facilitate parallel lead coiling around the pulse generator, prior to implantation of the pulse generator-secondary header-lead conglomerate into a previously prepared tissue pocket. Secondary header connector cavity 174 is for receipt of a DF-1 lead connector to replace the failed DF4 lead function disconnected at contact (HP) 186a as shown in connector cavity 172.

Figure 44B:
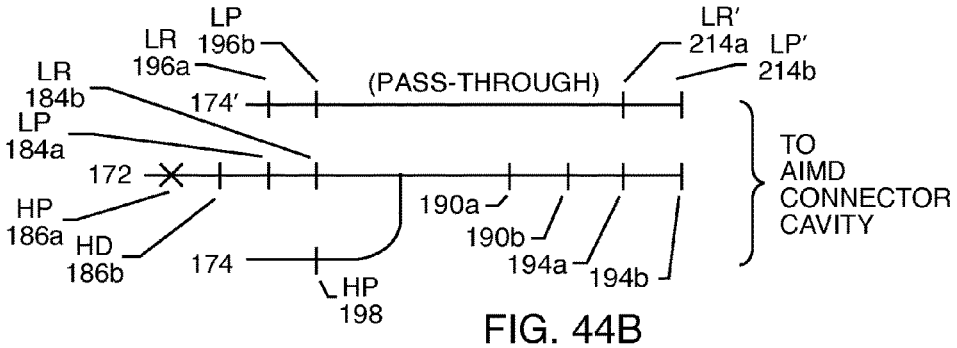
FIG. 44B is a line diagram taken from FIG. 44A illustrating which electrical connections are active and which are inactive.

FIG. 44B is an electrical line diagram taken generally from FIG. 44A further illustrating that the secondary header connector cavity 174' is a simple IS-1 pass-through and that connector cavity 174 provides a contact (HP) 198 for a new DF-1 high-voltage shocking lead (not shown). FIG. 44B also illustrates that the defective high-voltage shocking lead conductor that will appose contact (HP) 186a in connector cavity 172, following insertion of the partially failed DF4 lead connector therein, will have been disconnected from the DF4 secondary header connector plug 168, and thereby will be disconnected from AIMD electronics, following completion of all lead connections to the secondary header 160 and insertion of the secondary header's twin connector plugs 168, 168' into the appropriate pulse generator.

FIG. 45A includes a line diagram of the human heart 102 similar to that previously described in FIG. 5. Also shown is a CRT cardiac pacemaker 100, and a low profile secondary header 160 of the present invention. In this case, the secondary header 160 has one IS4 connector cavity 172 and four IS-1 connector cavities 174, 174', 174" and 174'", as required to correct a complete and total failure of the previously implanted IS4 lead 104'". The secondary header connector 168 is plugged into the same primary connector cavity in the header block 114, where the IS4 lead connector 104'" was previously plugged. Four new IS-1 leads 180, 180', 180" and 180'" are ready for connection to the IS-1 connector cavities 174, 174', 174" and 174'" of the secondary header 160, after being routed transthoracically, by one of a variety of limited thoracotomy or telescopic-plus port techniques, to sites on or near the epicardial surface of the left ventricle 136 shown as 216 through 216'". Transthoracic lead placement as described is often referred to as minimally invasive, at least compared to more major surgical procedures requiring the chest wall to be more widely opened through lateral or sternal incisions. The transthoracic leads may exit the chest wall at various locations and are then easily tunneled into the device pectoral or other pocket where their connectors can be conveniently plugged into the low profile secondary header 160.

Figure 45:
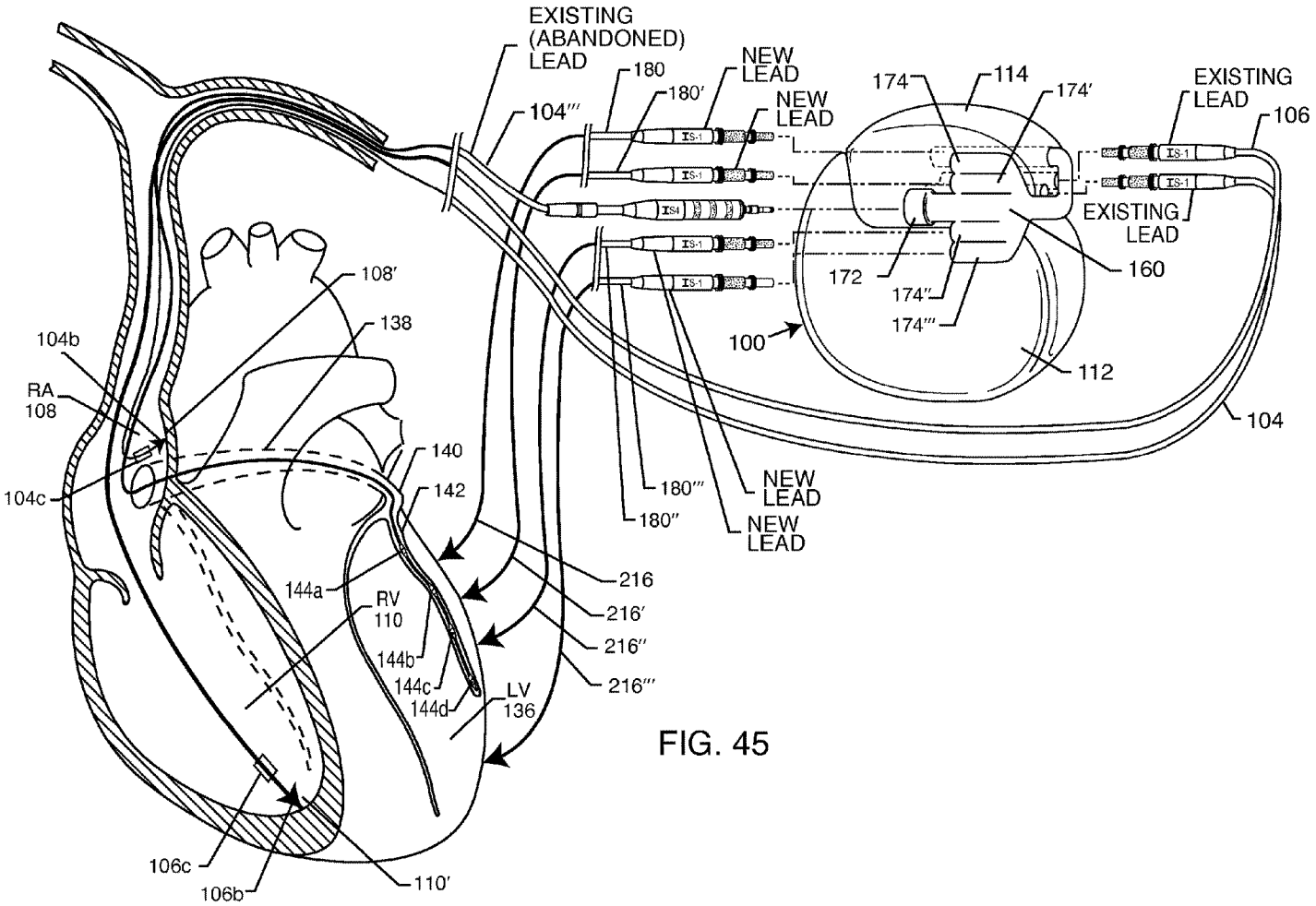
FIG. 45 illustrates an outlined drawing of a human heart with leads routed from a cardiac pacemaker 100C. This embodiment allows for the replacement of a dysfunctional IS4 lead with up to four unipolar leads terminating in epicardial or myocardial electrodes.
Figure 46A:
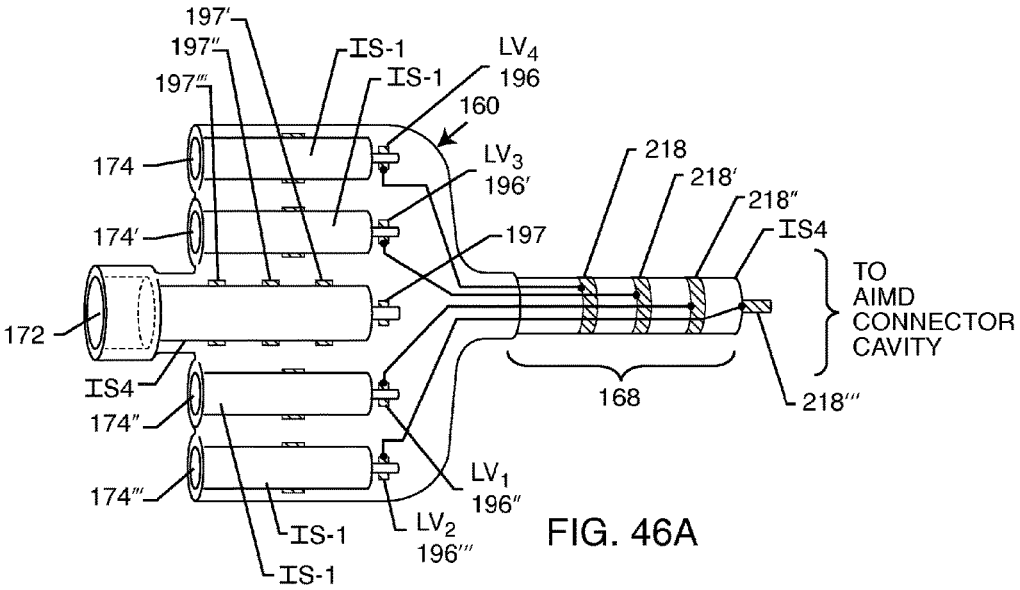
FIG. 46A illustrates a pictorial diagram of the low profile secondary header previously illustrated in FIG. 45 wherein one of the rings could function as a common ground to allow triple site stimulation.

FIG. 46A is a pictorial electrical wiring diagram taken from the secondary header 160 previously illustrated in FIG. 45. One can see that there is an IS4 connector plug 168 which is designed to be plugged into the AIMD connector cavity which was previously occupied by failed lead 104'" in FIG. 45. Shown are four IS-1 secondary header connector 160 cavities 174, 174', 174" and 174". Each of these has a unipolar electrical contact 196, 196', 196" and 196'" for engaging the tip electrode of an IS-1 lead. The four IS-1 contacts just described are then routed to ring contacts 218 through 218'" on secondary header connector plug 168. One can see that all of the contacts inside connector cavity 172 are disconnected from the secondary header's 160 connector plug 168, and so would not be connected to AIMD circuitry, even after plug 168 had been inserted into the AIMD connector cavity and the pin setscrew (not shown) appropriately tightened. In a particularly preferred embodiment, all four of these electrical contacts 197, 197', 197" and 197'" in the connector cavity 172 would be connected to an energy-dissipating surface 200 (not shown). In addition one of the ring electrodes on the connector 168, for example 218, could function as a ground, or even as a common ground to 174, 196 so that one or all three of the remaining secondary connector cavities, for example 174', 174" and 174'" could provide bipolar low voltage pacing and sensing (referenced to common ground 174 or to each other in any combination).

Figure 46B:
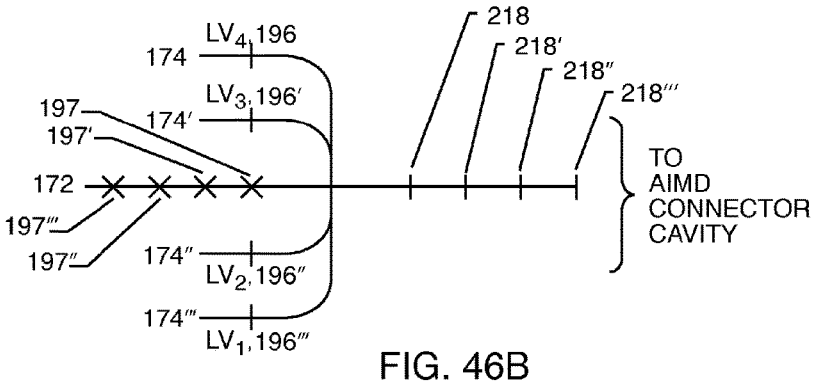
FIG. 46B is a line diagram taken from FIG. 46A illustrating which electrical contacts are active and which are inactive.

FIG. 46B is an electrical line diagram taken from FIG. 46A showing which electrical contacts are active and which are inactive. As one can see, all of the electrode contact sites 197, 197', 197" and 197'" within connector cavity 172 have been disconnected. It must also be understood that all four of the LV electrode stimulation sites 216 through 216'", as illustrated in FIG. 45, must be referenced to the associated metal pulse generator housing 112 to achieve a common ground and so called unipolar pacing and capture wherein the pulse generator housing is an electrode. The three alternative bipolar configurations described in the preceding paragraph would be far preferred, if the implanted pulse generator system included defibrillation functions, where bipolar sensing is considered of primary importance.

FIGS. 43 and 45 illustrate that the low profile secondary header 160 may have any number of secondary header connector plugs 168 and/or any number of secondary header connector cavities 172, 174, with an extensive range of electrical options limited only by the number of active and/or failed leads the patient presents with, additional leads required, and size and mechanical considerations. Further the present invention is not limited to just IS4 and DF4. As lead and other AIMD connectors continue to evolve, the low profile, compact, secondary header features, with no lead body like components; plus the total and permanent disconnection of all dysfunctional lead conductors and other components from the associated pulse generator features of the present invention, are adaptable to any new sizes, shapes or number of conductors in future connectors and the like. In addition, the compact, all elements maintained in the pocket features provide a new and distinct approach for replacement of and improvement over all prior model lead design based adaptors.

In general as illustrated in FIGS. 26A-29B, 42A-44B, as well as 46A and 46B, the functionality of the secondary header 160 of the present invention can be described in mathematical terms. The mathematical relationship correlates the active and inactive electrical contacts provided by the medical lead connector cavities, residing at the distal end portion of the secondary header, to the active electrical contacts of the secondary header plug residing at the proximal end portion of the secondary header. Therefore, the relationship between the electrical contacts of the distal end connector cavities of the secondary header to that of the proximal end plug of the secondary header can be defined by the mathematical equation:

$$X-S=N,$$

where X equals the total number of electrical connections provided by the medical leads, S equals the number of inactive electrical connections of the medical leads, and N equals the number of active electrical connections of the secondary header plug. It is contemplated that the number of active electrical connections N of the secondary header plug may reside within a multitude number of secondary header plugs. Furthermore, two or more medical leads may provide a plurality of active and inactive electrical connections.

Figure 47:
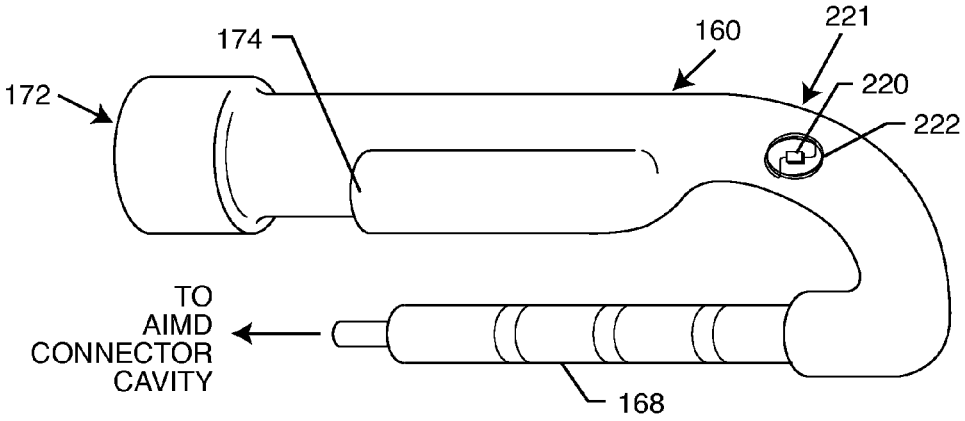
FIG. 47 illustrates that any of the low profile secondary headers previously illustrated may be fitted with an RFID chip and antenna.

FIG. 47 illustrates any of the low profile secondary header 160 illustrated in previous drawings fitted with an RFID chip 220 and RFID antenna 222. In general, this would form a passive RFID tag 221, meaning that it captures all of its energy from an external interrogator or RFID reader. The RFID tag 221 may be placed in any physical location on or within the low profile secondary header 160. In addition, it will be obvious that the low profile secondary header 160 may be slightly enlarged for a section to provide room for the RFID tag 221 including its associated chip 220 and antenna 222. U.S. Pat. No. 7,983,763 describes RFID tags for implanted leads. The contents of the '763 patent are incorporated herein by reference.

Figure 48:
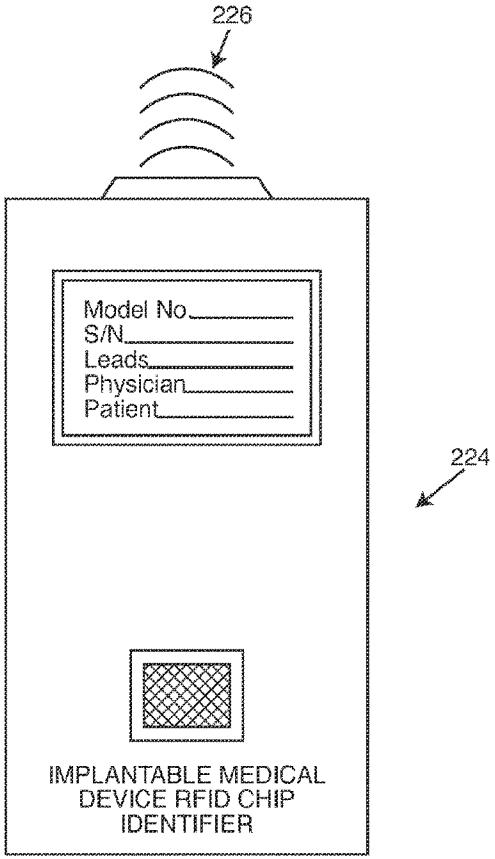
FIG. 48 illustrates an RFID reader interrogator.

FIG. 48 illustrates a handheld RFID reader interrogator 224, which provides an electromagnetic signal 226, which the antenna 222 of the RFID tag 221 captures as energy and uses to charge up an onboard capacitor. This capacitor (not shown) provides energy for the RFID chip 220 electronics so that the RFID tag 221 may emit a return pulse 228.

Figure 49:
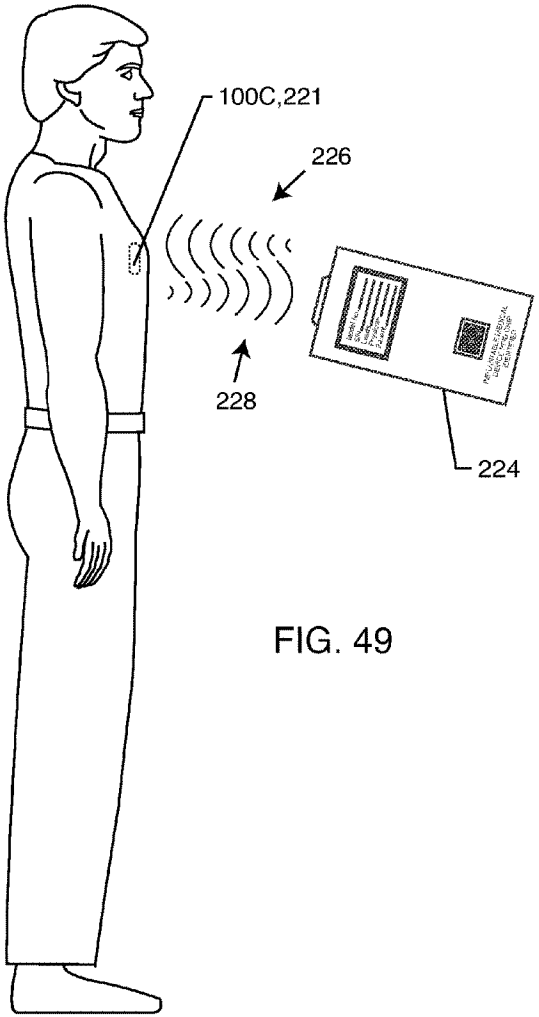
FIG. 49 illustrates the RFID reader of FIG. 48 being directed to read an RFID chip implanted in the secondary header of the present invention inside of a patient.

FIG. 49 illustrates the RFID reader 224 from FIG. 48 directed at a patient with an AIMD 100C. AIMD 100C is connected to a low profile secondary header (not shown) that includes an RFID tag 221 as previously illustrated in FIG. 47. The information stored on the RFID tag 221 should at a minimum include the date of manufacture, and the model and serial numbers of the secondary header 160 as well as the presence of an energy dissipating surface 200. It could also, with informed consent, include some aspects of the patient's medical history, details of the patient's pulse generator and lead system, including model numbers and lengths, MRI compatibility and an almost endless list of device related parameters and functions.

From the foregoing it will be appreciated that the present invention is broadly directed to a secondary header for an active implantable medical device (AIMD) incorporating a connector cavity having a plurality of electrical contacts. The secondary header comprises a secondary header plug configured for mating physical and electrical insertion into the AIMD connector cavity. The secondary header plug has a plurality of electrical contacts which correspond to the plurality of electrical contacts of the AIMD connector cavity. A secondary header connector cavity has the same physical dimensions as the AIMD connector cavity and one or more electrical contacts, but less than the number of secondary header plug electrical contacts, conductively coupled to respective secondary header plug electrical contacts. At least one replacement lead connector cavity has at least one electrical contact conductively coupled to at least one secondary header plug electrical contact.

In a preferred embodiment, the AIMD connector cavity comprises an ISO DF4 or IS4 connector cavity having four electrical contacts. The secondary header plug is configured for mating physical and electrical insertion into the AIMD ISO DF4 or IS4 connector cavity, and has four electrical contacts which correspond to the four electrical contacts of the AIMD ISO DF4 or IS4 connector cavity. The secondary header connector cavity comprises a secondary header ISO DF4 or IS4 connector cavity having less than four electrical contacts conductively coupled to the secondary header plug electrical contacts. In this case, the at least one replacement lead connector cavity incorporates an ISO IS-1 and/or DF-1 connector cavity.

The secondary header auxiliary plug may be configured for mating physical and electrical insertion into the AIMD ISO IS-1 or DF-1 connector cavity, and include a pass-through lead connector cavity having at least one electrical contact conductively coupled to at least one electrical contact on the secondary header auxiliary plug.

An intermediate conformal section is disposed between the secondary header plug and a housing for the secondary header connector cavity, for placing the secondary header connector cavity housing adjacent to an exterior surface of the AIMD. The secondary header connector cavity housing is typically spaced no more than 2 mm from the AIMD exterior surface, and the secondary header connector cavity housing has an exterior surface which tightly conforms to the adjacent AIMD exterior surface.

An energy dissipating surface may be electrically connected to one or more electrical contacts of the secondary header connector cavity which are not conductively coupled to the secondary header plug electrical contacts. The energy surface may be disposed on either an exterior surface of the housing for the secondary header connector cavity housing, or it may substantially encircle at least a portion of the secondary header connector cavity housing, or it may be disposed in a recess formed on the exterior surface of the secondary header connector cavity housing.

A diverter circuit may also be electrically connected between the energy dissipating surface and the one or more electrical contacts of the secondary header connector cavity which are not conductively coupled to the secondary header plug electrical contacts. The diverter circuit may comprise a short, a capacitor, an R-C circuit, an L-C trap, or an R-L-C circuit. Moreover, an RFID tag may be affixed or embedded within the secondary header.

In yet another embodiment, the secondary header connector cavity has no electrical contacts conductively coupled to any electrical contact on the secondary header plug. At least one of the secondary header connector cavity electrical contacts is electrically connected to an energy dissipating surface.

It will be obvious to those skilled in the art that a number of lead conductor failures have been illustrated as examples. There are many other combinations and permutations of conductor, connector, insulation, distal electrode, fixation mechanism and other component failures and dysfunctions of lead systems that this invention is equally applicable to. It will be obvious to those skilled in the art that the low profile secondary header of the present invention can be adapted to fit any combination of implanted lead component failure.

Although several embodiments of the invention have been described in detail for purposes of illustration, various modifications of each may be made without departing from the spirit and scope of the invention. Accordingly, the invention is not to be limited, except as by the appended claims.

What is claimed is:

1. A secondary header for an active implantable medical device (AIMD), the secondary header comprising:

a) a proximal electrical contact plug having four electrical contacts and being configured for mating physical and electrical insertion into the AIMD ISO DF4 or IS4 connector cavity;

b) a primary connector cavity having less than four to zero primary electrical contacts conductively coupled to respective ones of the four electrical contacts of the proximal electrical contact plug; and c) at least one replacement connector cavity having one to four replacement electrical contacts not provided by the primary connector cavity, the one to four replacement electrical contacts being conductively coupled to respective electrical contacts of the proximal electrical contact plug not conductively coupled to the less than four to zero primary electrical contacts of the primary connector cavity[.]*; and* d) *an energy dissipating surface electrically connected to from one to four primary electrical contacts of the primary connector cavity not conductively coupled to electrical contacts of the proximal electrical contact plug,*

*e*) wherein each of the four electrical contacts on the proximal electrical contact plug is either:

i) only conductively coupled to a respective one of the less than four to zero primary contacts of the primary connector cavity, or ii) only conductively coupled to a respective one of the one to four replacement electrical contacts of the replacement connector cavity.

2. The secondary header of claim 1, wherein the at least one replacement connector cavity incorporates an ISO IS-1 and/or a DF-1 connector cavity having one or two electrical contacts.

3. The secondary header of claim 1, having a low profile conforming shape including an intermediate conformal section between the proximal electrical contact plug and the primary and replacement connector cavities, wherein the low profile conforming shape is adapted for placing the secondary header adjacent to an exterior surface of an AIMD when the proximal electrical contact plug is placed within the AIMD connector cavity.

[4. The secondary header of claim 1, including an energy dissipating surface electrically connected to from one to four primary electrical contacts of the primary connector cavity not conductively coupled to electrical contacts of the proximal electrical contact plug.]

5. The secondary header of claim [4] *1*, wherein[.] the energy dissipating surface is disposed on an exterior surface of the secondary header.

6. The secondary header of claim 5, wherein the energy dissipating surface substantially encircles at least a portion of the primary and replacement connector cavities.

7. The secondary header of claim 5, wherein the energy dissipating surface is disposed in a recess formed on the exterior surface of the secondary header.

8. The secondary header of claim [4] *1*, including a diverter circuit electrically connected between the energy dissipating surface and the from one to four primary electrical contacts of the primary connector cavity not conductively coupled to electrical contacts of the proximal electrical contact plug.

9. The secondary header of claim 8, wherein the diverter circuit is selected from the group consisting of a short, a capacitor, an R-C circuit, an L-C trap, and an R-L-C circuit.

10. The secondary header of claim 1, including an RFID tag affixed to or embedded within the secondary header.

11. The secondary header of claim 1, wherein the primary connector cavity has no primary electrical contacts conductively coupled to any replacement electrical contact of the replacement connector cavity.

12. The secondary header of claim 11, wherein at least one of the primary electrical contacts of the primary connector cavity is electrically connected to an energy dissipating surface.

13. The secondary header of claim 1 wherein the primary and replacement connector cavities are positioned side-by-side.

14. A secondary header connectable to an active implantable medical device (AIMD) incorporating a connector cavity having a plurality of electrical contacts, the secondary header comprising:

a) a secondary header plug configured for mating physical and electrical insertion into an AIMD connector cavity, *wherein the secondary header plug has a plurality of electrical contacts which correspond to the plurality of electrical contacts of the AIMD connector cavity*;

b) a secondary header connector cavity disposed within a housing and having at least one electrical contact conductively coupled to a respective at least one electrical contact on the secondary header plug, *wherein the secondary header connector cavity has the same physical dimensions as the AIMD connector cavity, and one or more electrical contacts, but less than the number of secondary header plug electrical contacts, conductively coupled to respective secondary header plug electrical contacts*; [and]

c) an intermediate conformal section between the secondary header plug and the secondary header connector cavity housing, for placing the secondary header connector cavity housing adjacent to an exterior surface of an AIMD when the secondary header plug is placed within an AIMD connector cavity*; and*

*d) at least one replacement lead connector cavity having at least one electrical contact conductively coupled to at least one secondary header plug electrical contact.*

15. The secondary header of claim 14, wherein the secondary header connector cavity housing is spaced no more than 2 mm from the AIMD exterior surface.

16. The secondary header of claim 14, wherein the secondary header connector cavity housing has an exterior surface which tightly conforms to the adjacent AIMD exterior surface.

17. The secondary header of claim 14, [including] *wherein the* at least one replacement lead connector cavity *resides* within the secondary header connector cavity housing[, the replacement lead connector cavity having at least one electrical contact conductively coupled to a respective at least one electrical contact on the secondary header plug].

18. The secondary header of claim 14, including an RFID tag affixed to or embedded within the secondary header.

[19. The secondary header of claim 14, wherein:

a) the secondary header plug has a plurality of electrical contacts which correspond to the plurality of electrical contacts of the AIMD connector cavity;

b) the secondary header connector cavity has the same physical dimensions as the AIMD connector cavity, and one or more electrical contacts, but less than the number of secondary header plug electrical contacts, conductively coupled to respective secondary header plug electrical contacts; and c) including at least one replacement lead connector cavity having at least one electrical contact conductively coupled to at least one secondary header plug electrical contact.]

20. The secondary header of claim [19] *14*, wherein the AIMD connector cavity comprises an ISO DF4 or IS4 connector cavity having four electrical contacts, wherein the secondary header plug is configured for mating physical and electrical insertion into the AIMD ISO DF4 or IS4 connector cavity, the secondary header plug having four electrical contacts which correspond to the four electrical contacts of the AIMD ISO DF4 or IS4 connector cavity, and wherein the secondary header connector cavity comprises a secondary header ISO DF4 or IS4 connector cavity having less than four electrical contacts conductively coupled to the secondary header plug electrical contacts.

21. The secondary header of claim 20, including a secondary header auxiliary plug configured for mating physical and electrical insertion into an AIMD ISO IS-1 or DF-1 connector cavity, and a pass-through lead connector cavity having at least one electrical contact conductively coupled to at least one electrical contact on the secondary header auxiliary plug.

22. The secondary header of claim 20, wherein the at least one replacement lead connector cavity incorporates one or more ISO IS-1 and/or DF-1 connector cavities.

23. The secondary header of claim [19] *14*, including an energy dissipating surface electrically connected to one or more electrical contacts of the secondary header connector cavity which are not conductively coupled to the secondary header plug electrical contacts.

24. The secondary header of claim 23, wherein the energy dissipating surface is either disposed on an exterior surface of a housing for the secondary header connector cavity housing, substantially encircles at least a portion of the secondary header connector cavity housing, or is disposed in a recess formed on the exterior surface of the secondary header connector cavity housing.

25. The secondary header of claim 23, including a diverter circuit electrically connected between the energy dissipating surface and the one or more electrical contacts of the secondary header connector cavity which are not conductively coupled to the secondary header plug electrical contacts.

26. The secondary header of claim 25, wherein the diverter circuit is selected from the group consisting of a short, a capacitor, an R-C circuit, an L-C trap, and an R-L-C circuit.

27. The secondary header of claim 20, wherein the secondary header ISO DF4 or IS4 connector cavity has no electrical contacts conductively coupled to any electrical contact on the secondary header plug.

28. The secondary header of claim 27, wherein at least one of the secondary header ISO DF4 or IS4 connector cavity electrical contacts is electrically disconnected from AIMD electronics while being electrically connected to an energy dissipating surface.

29. A secondary header that is connectable to a medical device, the secondary header comprising:

a) at least a first connector cavity configured to receive and electrically connect to a first medical lead and a second connector cavity configured to receive and electrically connect to a second medical lead, b) wherein X equals four, which comprises the number of electrical contacts provided by the first medical lead permanently connected to the first connector cavity, c) wherein Y comprises the number of electrical contacts provided by the first medical lead that are inactive, and d) wherein S comprises the number of active electrical contacts provided by the second medical lead permanently connected to the second connector cavity, such that S =Y, and S and Y are less than or equal to X and X is four; and e) a secondary header plug permanently conductively coupled to the first and second connector cavities and having four electrical contacts defined by the equation (X−Y)+S =4, wherein the secondary header plug is adapted to be positioned within and electrically coupled to a connector port of a header block of a medical device[.]; *and* f) *an energy dissipating surface electrically connected to from one to four primary electrical contacts of the primary connector cavity not conductively coupled to electrical contacts of the proximal electrical contact plug,* g) wherein each of the four electrical contacts on the secondary header plug is either:

i) only conductively coupled to a respective one of the X−Y electrical contacts of the first connector cavity, or ii) only conductively coupled to the S electrical contacts of the second connector cavity.

30. The secondary head of claim 29, wherein the secondary header plug and the connector port comply with ISO standard DF4 and IS4.

31. The secondary header of claim 29, wherein an active electrical connection of the second medical lead substitutes for a dysfunctional electrical connection of the first medical lead.

32. The secondary header of claim 29, wherein the active electrical contacts of the first and second medical leads are electrically connected to respective ones of the active electrical contacts of the secondary header plug.

33. A secondary header that is connectable to an active implantable medical device (AIMD), the secondary header comprising:

a) a proximal electrical contact plug having X electrical contacts and being configured for mating physical and electrical insertion into a connector cavity of an implantable medical device;

b) a primary connector cavity having Y, which is less than X, primary electrical contact or contacts permanently conductively coupled to respective ones of the X electrical contacts of the proximal electrical contact plug; and c) at least one replacement connector cavity having N replacement electrical contact or contacts being the difference between the X electrical contacts of the proximal electrical contact plug less the Y primary electrical contact or contacts of the primary connector cavity, the N replacement contact or contacts being permanently conductively coupled to electrical contact or contacts of the proximal electrical contact plug not permanently conductively coupled to the Y primary electrical contact or contacts of the primary connector cavity[.]; *and* d) *at least one energy dissipating surface electrically connected to the Y primary electrical contact or contacts of the primary connector cavity not permanently conductively coupled to the X electrical contacts of the proximal electrical contact plug;*

*e*) wherein each of the X electrical contacts on the proximal electrical contact plug is either:

i) only conductively coupled to a respective one of the Y primary contacts of the primary connector cavity, or ii) only conductively coupled to a respective one of the N electrical contacts of the replacement connector cavity.

34. The secondary header of claim 33 wherein when Y equals zero, X equals N.

35. The secondary header of claim 33 wherein the replacement connector cavity incorporates at least one ISO IS-1 and/or a DF-1 connector cavity.

36. The secondary header of claim 33 having a low profile conforming shape including an intermediate conformal section between the proximal electrical contact plug and the primary and replacement connector cavities, wherein the low profile conforming shape is adapted for placing the secondary header adjacent to an exterior surface of an AIMD when the proximal electrical contact plug is placed within the AIMD connector cavity.

[37. The secondary header of claim 33 including at least one energy dissipating surface electrically connected to the Y primary electrical contact or contacts of the primary connector cavity not permanently conductively coupled to the X electrical contacts of the proximal electrical contact plug.]

38. The secondary header of claim [37] *33* wherein the energy dissipating surface is disposed on an exterior surface of the secondary header.

39. The secondary header of claim [37] *33* wherein the energy dissipating surface substantially encircles at least a portion of the primary and replacement connector cavities.

40. The secondary header of claim [37] *33* wherein the energy dissipating surface is disposed in a recess formed on the exterior surface of the secondary header.

41. The secondary header of claim [37] *33* including at least one diverter circuit electrically connected between the at least one energy dissipating surface and the Y primary electrical contact or contacts of the primary connector cavity not conductively coupled to the X electrical contacts of the proximal electrical contact plug.

42. The secondary header of claim 41 wherein the diverter circuit is selected from the group consisting of a short, a capacitor, an R-C circuit, an L-C trap, and an R-L-C circuit.

43. The secondary header of claim 33 including an RFID tag affixed to or embedded within the secondary header.

44. The secondary header of claim [43] *33* wherein the primary and replacement connector cavities are positioned side-by-side.

*45. The secondary header of claim 1, wherein the energy dissipating surface is of stainless steel or titanium.*

*46. The secondary header of claim 29, wherein the energy dissipating surface is of stainless steel or titanium.*

*47. The secondary header of claim 33, wherein the energy dissipating surface is of stainless steel or titanium.*

* * * * *